(12) United States Patent
Efimov et al.

(10) Patent No.: US 9,067,079 B2
(45) Date of Patent: *Jun. 30, 2015

(54) METHOD FOR LOW-VOLTAGE TERMINATION OF CARDIAC ARRHYTHMIAS BY EFFECTIVELY UNPINNING ANATOMICAL REENTRIES

(71) Applicant: Washington University, St. Louis, MO (US)

(72) Inventors: Igor R. Efimov, Wildwood, MO (US); Valentin I. Krinski, Villeneuve Loubet (FR); Vladmir P. Nikolski, St. Anthony, MN (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/165,230

(22) Filed: Jan. 27, 2014

(65) Prior Publication Data

US 2014/0371804 A1 Dec. 18, 2014

Related U.S. Application Data

(60) Continuation of application No. 13/464,537, filed on May 4, 2012, now Pat. No. 8,639,325, which is a division of application No. 11/266,755, filed on Nov. 3, 2005, now Pat. No. 8,175,702.

(60) Provisional application No. 60/624,978, filed on Nov. 4, 2004, provisional application No. 60/697,858, filed on Jul. 7, 2005.

(51) Int. Cl.
*A61N 1/00* (2006.01)
*A61N 1/39* (2006.01)
(Continued)

(52) U.S. Cl.
CPC ............. *A61N 1/3906* (2013.01); *A61B 5/0464* (2013.01); *A61N 1/3627* (2013.01); *A61B 5/0402* (2013.01); *A61N 1/39* (2013.01); *A61B 5/7239* (2013.01); *A61N 1/3962* (2013.01)

(58) Field of Classification Search
USPC .................................................. 607/5, 14, 25
See application file for complete search history.

(56) References Cited

U.S. PATENT DOCUMENTS

| 3,729,008 A | 4/1973 | Berkovits |
| 3,738,370 A | 6/1973 | Charms |

(Continued)

FOREIGN PATENT DOCUMENTS

| AU | 2008335087 B2 | 2/2014 |
| AU | 2011248794 B2 | 3/2014 |

(Continued)

OTHER PUBLICATIONS

Davidenko et al., "Stationary and drifting spiral waves of excitation in isolated cardiac muscle," Nature, vol. 355, pp. 349-351, Jan. 23, 1992.

(Continued)

*Primary Examiner* — Nicole F Lavert
(74) *Attorney, Agent, or Firm* — Patterson Thuente Pedersen, P.A.

(57) ABSTRACT

A method for extinguishing a cardiac arrhythmia utilizes destructive interference of the passing of the reentry wave tip of an anatomical reentry through a depolarized region created by a relatively low voltage electric field in such a way as to effectively unpin the anatomical reentry. Preferably, the relatively low voltage electric field is defined by at least one unpinning shock(s) that are lower than an expected lower limit of vulnerability as established, for example, by a defibrillation threshold test. By understanding the physics of the electric field distribution between cardiac cells, the method permits the delivery of an electric field sufficient to unpin the core of the anatomical reentry, whether the precise or estimated location of the reentry is known or unknown and without the risk of inducting ventricular fibrillation. A number of embodiments for performing the method are disclosed.

12 Claims, 17 Drawing Sheets

(51) Int. Cl.
*A61N 1/362* (2006.01)
*A61B 5/0402* (2006.01)
*A61B 5/0464* (2006.01)
*A61B 5/00* (2006.01)

(56) References Cited

U.S. PATENT DOCUMENTS

| | | |
|---|---|---|
| 3,942,536 A | 3/1976 | Mirowski et al. |
| 4,136,703 A | 1/1979 | Wittkampf |
| 4,384,585 A | 5/1983 | Zipes |
| 4,727,877 A | 3/1988 | Kallok |
| 5,107,834 A | 4/1992 | Ideker et al. |
| 5,199,429 A | 4/1993 | Kroll et al. |
| 5,265,600 A | 11/1993 | Adams et al. |
| 5,275,621 A | 1/1994 | Mehra |
| 5,282,836 A | 2/1994 | Kreyenhagen et al. |
| 5,306,291 A | 4/1994 | Kroll et al. |
| 5,330,509 A | 7/1994 | Kroll et al. |
| 5,334,219 A | 8/1994 | Kroll |
| 5,365,391 A | 11/1994 | Sugiyama et al. |
| 5,372,605 A | 12/1994 | Adams et al. |
| 5,383,907 A | 1/1995 | Kroll |
| 5,387,613 A | 2/1995 | Goldberg et al. |
| 5,391,186 A | 2/1995 | Kroll et al. |
| 5,403,356 A | 4/1995 | Hill et al. |
| 5,405,363 A | 4/1995 | Kroll |
| 5,407,444 A | 4/1995 | Kroll |
| 5,413,591 A | 5/1995 | Knoll |
| 5,433,729 A | 7/1995 | Adams et al. |
| 5,489,293 A | 2/1996 | Pless et al. |
| 5,545,182 A | 8/1996 | Stotts et al. |
| 5,545,204 A | 8/1996 | Cammilli et al. |
| 5,562,708 A | 10/1996 | Combs et al. |
| 5,620,464 A | 4/1997 | Kroll et al. |
| 5,620,468 A | 4/1997 | Mongeon et al. |
| 5,674,248 A | 10/1997 | Kroll et al. |
| 5,676,687 A | 10/1997 | Ayers |
| 5,683,429 A | 11/1997 | Mehra |
| 5,766,226 A | 6/1998 | Pedersen |
| 5,792,187 A | 8/1998 | Adams |
| 5,797,967 A | 8/1998 | KenKnight |
| 5,813,999 A | 9/1998 | Ayers et al. |
| 5,840,079 A | 11/1998 | Warman et al. |
| 5,925,066 A | 7/1999 | Kroll et al. |
| 5,928,270 A | 7/1999 | Ramsey, III |
| 5,995,871 A | 11/1999 | Knisley |
| 6,070,081 A | 5/2000 | Takahashi et al. |
| 6,081,746 A | 6/2000 | Pendekanti et al. |
| 6,085,116 A | 7/2000 | Pendekanti et al. |
| 6,085,119 A | 7/2000 | Scheiner et al. |
| 6,091,991 A | 7/2000 | Warren |
| 6,094,596 A | 7/2000 | Morgan |
| 6,141,588 A | 10/2000 | Cox et al. |
| 6,157,859 A | 12/2000 | Alt |
| 6,178,351 B1 | 1/2001 | Mower |
| 6,185,459 B1 | 2/2001 | Mehra et al. |
| 6,205,357 B1 | 3/2001 | Ideker et al. |
| 6,233,483 B1 | 5/2001 | Causey, III et al. |
| 6,246,906 B1 | 6/2001 | Hsu et al. |
| 6,292,691 B1 | 9/2001 | Pendekanti et al. |
| 6,327,500 B1 | 12/2001 | Cooper et al. |
| 6,463,330 B1 | 10/2002 | Rabinovitch et al. |
| 6,510,342 B1 | 1/2003 | Park et al. |
| 6,526,317 B2 | 2/2003 | Hsu et al. |
| 6,556,862 B2 | 4/2003 | Hsu et al. |
| 6,567,698 B2 | 5/2003 | Herleikson |
| 6,587,720 B2 | 7/2003 | Hsu et al. |
| 6,711,442 B1 | 3/2004 | Swerdlow et al. |
| 6,745,081 B1 | 6/2004 | Helland et al. |
| 6,754,525 B1 | 6/2004 | Province et al. |
| 6,763,266 B1 | 7/2004 | Kroll |
| 6,813,516 B2 | 11/2004 | Ujhelyi et al. |
| 6,847,842 B1 | 1/2005 | Rodenhiser et al. |
| 6,937,896 B1 | 8/2005 | Kroll |
| 7,006,867 B1 | 2/2006 | Kroll |
| 7,020,517 B2 | 3/2006 | Weiner |
| 7,047,071 B2 | 5/2006 | Wagner et al. |
| 7,079,891 B1 | 7/2006 | Kroll |
| 7,110,811 B2 | 9/2006 | Wagner et al. |
| 7,113,822 B1 | 9/2006 | Kroll |
| 7,120,490 B2 | 10/2006 | Chen et al. |
| 7,127,292 B2 | 10/2006 | Warman et al. |
| 7,139,611 B1 | 11/2006 | Kroll et al. |
| 7,142,927 B2 | 11/2006 | Benser et al. |
| 7,142,928 B2 | 11/2006 | Sharma et al. |
| 7,155,286 B1 | 12/2006 | Kroll et al. |
| 7,181,276 B1 | 2/2007 | Province et al. |
| 7,480,351 B2 | 1/2009 | Hiatt, Jr. et al. |
| 7,532,933 B2 | 5/2009 | Hastings et al. |
| 7,647,109 B2 | 1/2010 | Hastings et al. |
| 7,848,823 B2 | 12/2010 | Drasler et al. |
| 7,899,537 B1 | 3/2011 | Kroll et al. |
| 7,925,343 B1 | 4/2011 | Min et al. |
| 8,032,218 B2 | 10/2011 | Wong et al. |
| 8,175,702 B2 | 5/2012 | Efimov et al. |
| 8,204,605 B2 | 6/2012 | Hastings et al. |
| 8,509,889 B2 | 8/2013 | Efimov et al. |
| 8,560,066 B2 | 10/2013 | Efimov et al. |
| 8,639,325 B2 | 1/2014 | Efimov et al. |
| 8,706,216 B2 | 4/2014 | Efimov et al. |
| 8,874,208 B2 | 10/2014 | Efimov et al. |
| 2001/0014816 A1 | 8/2001 | Hsu et al. |
| 2002/0128565 A1 | 9/2002 | Rudy |
| 2003/0083727 A1 | 5/2003 | Casavant et al. |
| 2003/0130703 A1 | 7/2003 | Florio et al. |
| 2003/0220676 A1 | 11/2003 | Helland |
| 2004/0111123 A1 | 6/2004 | Ware et al. |
| 2005/0096701 A1 | 5/2005 | Donovan et al. |
| 2005/0154420 A1 | 7/2005 | Diaz et al. |
| 2006/0161206 A1 | 7/2006 | Efimov et al. |
| 2007/0021793 A1 | 1/2007 | Voegele et al. |
| 2007/0088395 A1 | 4/2007 | Province et al. |
| 2009/0062877 A1 | 3/2009 | Krinski et al. |
| 2009/0204164 A1 | 8/2009 | Efimov et al. |
| 2010/0016917 A1 | 1/2010 | Efimov et al. |
| 2011/0009916 A1 | 1/2011 | Efimov et al. |
| 2011/0029032 A1 | 2/2011 | Bardy et al. |
| 2012/0203297 A1 | 8/2012 | Efimov et al. |
| 2012/0209343 A1 | 8/2012 | Efimov et al. |
| 2013/0013012 A1 | 1/2013 | Efimov et al. |

FOREIGN PATENT DOCUMENTS

| | | |
|---|---|---|
| CN | 103002948 A | 3/2013 |
| CN | 200880126712.0 | 12/2013 |
| EP | 0393265 A1 | 10/1990 |
| EP | 1062971 A1 | 12/2000 |
| EP | 2231263 A2 | 9/2010 |
| EP | 2566578 A2 | 3/2013 |
| GB | 2025236 A | 1/1980 |
| JP | 5421286 | 11/2013 |
| WO | WO 96/11035 A1 | 4/1996 |
| WO | WO 2006/042295 A1 | 4/2006 |
| WO | WO 2006/052838 A2 | 5/2006 |
| WO | WO 2008/063498 A1 | 5/2008 |

OTHER PUBLICATIONS

Gray et al., "Spatial and temporal organization during cardiac fibrillation," Nature, vol. 392, pp. 75-78, May 14, 1998.

Witkowski et al, "Spatiotemporal evolution of ventricular fibrillation," Nature, vol. 392, pp. 78-82, Mar. 5, 1998.

Cherry et al, "Visualization of spiral and scroll waves in simulated and experimental cardiac tissue", New J. Phys., vol. 10, pp. 125016-125059, 44 pages, 2008.

Koster et al., "A randomized trial comparing monophasic and biphasic waveform shocks for external cardioversion of atrial fibrillation," Am. Heart. J. vol. 147, pp. e1-e7, 2004.

Babbs et al., "Therapeutic indices for transchest defibrillator shocks: Effective, damaging, and lethal electrical doses," Am. Heart. J., vol. 99, No. 6, pp. 734-738, Jun. 1980.

(56) References Cited

OTHER PUBLICATIONS

Santini et al., "Single Shock Endocavitary Low Energy Intracardiac Cardioversion of Chronic Atrial Fibrillation," J. Interv. Card. Electrophysiol., vol. 3, pp. 45-51, 1999.
Sakurai et al., "Design and Control of Wave Propagation Patterns in Excitable Media," Science, vol. 296, pp. 2009-2012, Jun. 14, 2002.
Rappel et al, "Spatiotemporal Control of Wave Instabilities in Cardiac Tissue," Phys. Rev. Lett., vol. 83, No. 2, pp. 456-459, Jul. 12, 1999.
Fenton et al., "Multiple mechanisms of spiral wave breakup in a model of cardiac electrical activity," Chaos, vol. 12, No. 3, pp. 852-892, Sep. 2002.
Fenton et al., "Vortex dynamics in three-dimensional continuous myocardium with fiber rotation: Filament instability and fibrillation," Chaos, vol. 8, No. 1, pp. 20-47, Mar. 1998.
Mackenzie, "Making sense of a heart gone wild," Science, vol. 303, pp. 786-787, Feb. 6, 2004.
Walcott et al., "Do clinically relevant transthoracic defibrillation energies cause myocardial damage and dysfunction?" Resuscitation, vol. 59, pp. 59-70, 2003.
Fenton et al., "Termination of Atrial Fibrillation Using Pulsed Low-Energy Far-Field Stimulation," Circulation, vol. 120, pp. 467-476, 2009.
Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.
Plonsey, "The Nature of Sources of Bioelectric and Biomagnetic Fields," Biophys. J., vol. 39, pp. 309-312, 1982.
Sambelashvili et al., "Virtual electrode theory explains pacing threshold increase caused by cardiac tissue damage," Am. J. Physiol. Heart Circ. Physiol., vol. 286, pp. H2183-H2194, 2004.
Hooks et al, "Cardiac Microstructure: Implications for Electrical Propagation and Defibrillation in the Heart," Circ. Res., vol. 91, pp. 331-338, 2002.
Trayanova et al., "Modeling Defibrillation: Effects of Fiber Curvature," J. Electrocardiol., vol. 31 (suppl.), pp. 23-29, 1998.
Roth et al., "A Bidomain Model for the Extracellular Potential and Magnetic Field of Cardiac Tissue," IEEE Trans. Biomed. Eng., vol. 33, No. 4, pp. 467-469, Apr. 1986.
Murray, "The Physiological Principle of Minimum Work: I. The Vascular System and the Cost of Blood Volume," Proc. Natl. Acad. Sci. USA, vol. 12, pp. 207-214, 1926.
Kassab, "Scaling laws of vascular trees: of form and function," Am. J. Physiol. Heart Circ. Physiol., vol. 290, pp. H894-H903, 2006.
Maleckar et al., "Polarity reversal lowers activation time during diastolic field stimulation of the rabbit ventricles: insights into mechanisms," Am. J. Physiol. Heart Circ. Physiol., vol. 295, pp. H1626-H1633, 2008.
Kirchhof et al, "Regional entrainment of Atrial Fibrillation Studied by High-Resolution Mapping in Open-Chest Dogs," Circulation, vol. 88, pp. 736-749, 1993.
Pumir et al, "Wave Emission from Heterogeneities Opens a Way to Cotnrolling Chaos in the Heart," Phys. Rev. Lett., vol. 99, pp. 208101-1, 2007.
Gray et al, "Termination of spiral waves during cardiac fibrillation via shock-induced phase resetting," Proc. Natl. Acad. Sci. USA, vol. 102, No. 13, pp. 4672-4677, Mar. 29, 2005.
Gray et al., "Several small shocks beat one big one", vol. 475. Jul. 14, 2011. pp. 181-182.
Ladwig et al., "Absence of an Impact of Emotional Distress on the Perception of Intracardiac Shock Discharges," International Journal of Behavioral Medicine, 2003, 10(1):56-65, USA.
Fishler et al., "Spatiotemporal Effects of Syncytial Heterogeneities on Cardiac Far-field Excitations during Monophasic and Biphasic Shocks", Journal of Cardiovascular Electrophysiolgy, 1998, 9(12):1310-24, USA.
Efimov et al., "Virtual Electrode-Induced Phase Singularity: A Basic Mechanism of Defibrillation Failure," Circulation Research, 1998, 82(8):918-25, USA.
Efimov et al., "Transmembrane Voltage Changes Produced by Real and Virtual Electrodes During Monophasic Defibrillation Shock Delivered by an Implantable Electrode," Journal of Cardiovascular Electrophysiolgy, 1997, 8(9):1031-45, USA.
Cheng et al., "Virtual Electrode-Induced Reexcitation: A Mechanism of Defibrillation," Circulation Research, 1999, 85(11):1056-66, USA.
Fishler, "Syncytial Heterogeneity as a Mechanism Underlying Cardiac Far-Field Stimulation During Defibrillation-Level Shocks," Journal of Cardiovascular Electrophysiolgy, 1998, 9(4):384-94, USA.
Tsukerman et al., "Defibrillation of the Heart by a Rotating Current Field," Kardiologiia, 1973, 13(12):75-80, USA.
Zheng et al., "Reduction of the Internal Atrial Defibrillation Threshold with Balanced Orthogonal Sequential Shocks," Journal of Cardiovascular Electrophysiolgy, 2002; 13(9):904-9, USA.
Hucker et al., "Atrioventricular conduction with and without AV nodal delay: two pathways to the bundle of His in the rabbit heart", Am J. Physiol. Heart Circ. Physiol., 2007, 293:H1122-H1130, USA.
Mowrey et al., "Membrane Time Constant During Internal Defibrillation Strength Shocks in Intact Heart: Effects of Na.sup.+ and Ca.sup.2+ Channel Blockers," J. Cardiovascular Electrophysiology, Apr. 25, 2004, Jun. 8, 2008, and Jan. 2009, 20(1):85-92, USA.
Sepulveda et al., "Current injection into a two-dimensional anisotropic bidomain", Biophys. J., vol. 55, May 1989, pp. 987-999, USA.
Allessie et al., "Regional Control of Atrial Fibrillation by Rapid Pacing in Conscious Dogs", Circulation, vol. 84, No. 4, Oct. 1991, pp. 1689-1697, USA.
Daoud et al., "Response of Type I Atrial Fibrillation to Atrial Pacing in Humans", Circulation, vol. 94, No. 5, 1996, 13 pages, USA.
Disertori et al., "Antitachycardia pacing therapies to terminate atrial tachyarrhythmias: the AT500 Italian Registry", European Heart Journal Supplements, 2001, pp. 16-24, USA.
Pumir et al., "Unpinning of a Rotating Wave in Cardiac Muscle by an Electric Field", J. Theor. Biol., vol. 199, 1999, pp. 311-319, USA.
N. S. Peters et al., "Disturbed Connexin43 Gap Junction Distribution Correlates With the Location of Reentrant Circuits in the Epicardial Border Zone of Healing Canine Infarcts That Cause Ventricular Tachycardia," Circulation, 1997, 95:988-996.
J. T. Niemann et al., "Intracardiac Voltage Gradients during Transthoracic Defibrillation: Implications for Postshock Myocardial Injury," Acad. Emerg. Med., Feb. 2005, 12(2):99-105.
I. Kodama et al., "Aftereffects of high-intensity DC stimulation of the electromechanical performance of ventricular muscle", Am J. Physiol., 1994, 267:H248-H258.
H. G. Li et al., "Defribillation Shocks Produce Different Effects on Purkinje Fibers and Ventricular Muscle: Implications for Successful Defibrillation, Refibrillation and Postshock Arrhythmia", J Am Coll Cardiol, 1993, 22:607-614.
X. Zhou et al., "Epicardial Mapping of Ventricular Defibrillation With Monophasic and Biphasic Shocks in Dogs," Circulation Research, Jan. 1993, 72(1):145-160.
L. Li et al., "Mechanisms of enhanced shock-induced arrhythmogenesis in the rabbit heart with healed myocardial infarction," Am. J. Physiol. Heart Circ Physiol., May 3, 2005, 289:H1054-H1068.
A. Sambelashvili et al., "Nonlinear effects in subthreshold virtual electrode polarization," Am. J. Physiol. Heart Circ, Physiol., 2003, 284(6):H2368-H2374.
F. Aguel et al., "Advances in Modeling Cardiac Defibrillation," Int'l Journal of Bifurcation & Chaos, 2003, 13(12):3791-3803.
M. Hillebrenner et al., "Postshock arrhythmogenesis in a slice of the canine heart," J. Cardiovasc. Electrophys., 2003, 14:S249-S256.
N. Trayanova et al., "Virtual Electrode-Induced Positive and Negative Graded Responses: New Insights into Fibrillation Induction and Defibrillation," J. Cardiovascular Electrophysicology, 2003, 14(7):756-763.
C. Larson et al., "Analysis of Electrically-Induced Reentrant Circuits in a Sheet of Myocardium," Annals Biomed. Eng., 2003, 31:768-780.
I. R. Efimov, "Filbrillatin or Neurillation: Back to the future in our concepts of sudden cardiac death?", Circ. Res., May 30, 2003, 92(10):1062-1064.

(56) References Cited

OTHER PUBLICATIONS

I. R. Efimov et al., "Diastolic Shocking Experience: Do Virtual Anodes Exist Only During Systole?", J. Cardiovascular Electrophysiology, Nov. 2003, 14(11):1223-1224.

I. R. Efimov et al., Fast Fluorescent Mapping of Electrical Activity in the Heart: Practical Guide to Experimental Design and Applications, Chapter 7, pp. 131-156.

Y. Cheng et al., "Shock-induced arrhythmogenesis is enhanced by 2,3-butanedione monoxime compared with cytochalasin D," Am. J. Physiol. Heart Circ. Physiol., 2004, 286:H310-H318.

S. Takagi et al., "Unpinning and Removal of a Rotating Wave in Cardiac Muscle", Phys. Review Letters, Jul. 30, 2004, 93(5):058101-1-058101-4.

L. Li et al., "Effects of Lidocaine on Shock-Induced Vulnerability", J. Cardiovascular Electrophysiology, Oct. 2003, 14(10):S237-S248.

Y. Cheng et al., "Mechanisms of Shock-Induced Arrhythmogenesis During Acute Global Ischemia", Am J Physiol. Heart Circ. Physiol., Jun. 2002, 282(6):H2141-51.

F. Qu et al., "Mechanisms of Superiority of Ascending Ramp Waveforms: New Insights into Mechanisms of Shock-induced Vulnerability and Defibrillation," Am. J. Physiol. Heart Circ. Physiol., 2005, 289:H569-H577.

T. Ashihara et al., "Spiral Wave Control by a Localized Stimulus: A Bidomain Model Study," J. Cardiovascular Electrophysiology, Feb. 2004 15(2):226-233.

C. Ramanathan, "Noninvasive electrocardiographic imaging for cardiac electrophysiology and arrhythmia," Nature Medicine, Apr. 2004, 10(4):422-428.

V. Nikolski et al., "Fluorescent Imaging of a Dual-Pathway Atrioventricular-Nodal Conduction System," Circ Res., Feb. 16, 2001, pp. 1-8.

F. Qu et al., "The Gurvich waveform has lower defibrillation threshold than the Zoll waveform and the truncated exponential waveform in the rabbit heart," Can. J. Physiol. Pharmacol., 2005, 83:152-160.

Grosu et al., "Learning and Detecting Emergent Behavior in Networks of Cardiac Myocytes", Communications of the ACM, Mar. 2009, pp. 97-104, vol. 52, No. 3.

Ripplinger et al., "Mechanisms of unpinning and termination of ventricular tachycardia", Am J. Physiol. Heart Circ. Physiol., 2006, pp. H184-H192.

Cartee et al., "The Transient Subthreshold Response of Spherical and Cylindrical Cell Models to Extracellular Stimulation", IEEE Trans. Biomed. Eng., vol. 39, No. 1, Jan. 1992, pp. 76-85.

Ideker et al., "Correlation Among Fibrillation, Defibrillation and Cardiac Pacing", Pacing Clin. Electrophysiol., vol. 18, Mar. 1995, pp. 512-525.

Sobie et al., "A Generalized Activating Function for Predicting Virtual Electrodes in Cardiac Tissue", Biophys. J., vol. 73, Sep. 1997, pp. 1410-1423.

Trayanova et al., "The Response of a Spherical Heart to a Uniform Electric Field: A Bidomain Analysis of Cardiac Stimulation", J. IEEE trans. Biomed. Eng., vol. 40, No. 9, Sep. 1993, pp. 899-908.

Chebbok et al., Low Energy Anti-Fibrillation Pacing (LEAP): A Gental, non traumatic defibrillation Option. European Heart Journal 33: 381-381 Suppl. 1, Aug. 2012.

PCT/US2005/040187 Search Report dated Apr. 21, 2008, 3 pages.

PCT/US2005/040187 Written Opinion dated Apr. 21, 2008, 4 pages.

International Preliminary Report; PCT/US2005/040187; dated Feb. 24, 2009, 5 pages.

European Office Action for European Application No. 05825356.8 dated Jun. 6, 2014, 4 pages.

European Response for European Application No. 058253568 dated Jan. 5, 2015, 22 pages.

Application and File History for U.S. Appl. No. 12/776,196, filed May 7, 2010, now U.S. Patent No. 8,560,066. Inventor: Efimov et al.

Application and File History for U.S. Appl. No. 12/518,343, filed Sep. 2, 2009, now U.S. Patent No. 8,391,995. Inventors: Efimov et al.

Application and File History for U.S. Appl. No. 12/333,257, filed Dec. 11, 2008, now U.S. Patent No. 8,509,889. Inventors: Efimov et al.

Application and File History for U.S. Appl. No. 11/266,755, filed Nov. 3, 2005, now U.S. Patent No. 8,175,702. Inventors: Efimov et al.

Application and File History for U.S. Appl. No. 13/464,537, filed May 4, 2012, now U.S. Patent No. 8,639,325. Inventors: Efimov et al.

Application and File History for U.S. Appl. No. 13/349,527, filed Jan. 12, 2012, now U.S. Patent No. 8,874,208. Inventors: Efimov et al.

Application and File History for U.S. Appl. No. 13/349,517, filed Jan. 12, 2012, now U.S. Patent No. 8,706,216. Inventors: Efimov et al.

FIG. 2

METHOD FOR LOW-VOLTAGE TERMINATION OF CARDIAC ARRHYTHMIAS BY EFFECTIVELY UNPINNING ANATOMICAL REENTRIES

RELATED APPLICATION

This application is a continuation of application Ser. No. 13/464,537, filed May 4, 2012 and now issued as U.S. Pat. No. 8,639,325, which is a division of application Ser. No. 11/266,755 filed Nov. 3, 2005, now issued as U.S. Pat. No. 8,175,702, which claims the benefit of U.S. Provisional Application No. 60/624,978, filed Nov. 4, 2005, and of U.S. Provisional Application No. 60/697,858, filed Jul. 7, 2005, each of which is hereby fully incorporated herein by reference.

FIELD OF THE INVENTION

The present invention relates generally to a method for termination of cardiac arrhythmias and, more specifically, to a method for extinguishing an arrhythmia by destructive interference of the passing of the reentry wave tip of an anatomical reentry through a depolarized region created by a relatively low voltage electric field in such a way as to effectively unpin the anatomical reentry.

BACKGROUND OF THE INVENTION

It is well-known that rotating waves of electrical activity are a factor in potentially dangerous cardiac arrhythmias such as ventricular tachycardias and ventricular fibrillations ("ventricular tachycardia events"). The rotating waves, or reentries, that are responsible for ventricular tachycardia events are classified into two categories: 1) functional reentries, which involve freely rotating waves; and 2) anatomical reentries, where a wave rotates around an obstacle such as a blood vessel or piece of ischemic tissue. The latter are referred to as being 'pinned' by the obstacle. Traditional defibrillation is not a preferred way of dealing with such rotating waves because defibrillation resets electrical activity everywhere in the heart and uses high voltage shocks, which have undesirable side effects.

One common method of attempting to terminate these rotating waves or reentries is antitachycardia pacing (ATP). ATP has a high rate of success in dealing with functional reentries, but is not as effective against anatomical reentries. Generally, if ATP is not effective, a defibrillating shock of large amplitude is applied directly to cardiac muscle.

The reasons ATP is not always successful can be found in the complexity of the system. In one-dimension, the situation involving reentries is well-understood and relatively simple. A reentry essentially consists of a pulse rotating along a closed ring. To terminate a reentry, it is enough to deliver a stimulus close to the tail of the rotating pulse. The stimulus should be delivered inside the critical time interval (the so-called vulnerable window, VW). Under these circumstances, only one pulse is created and it propagates in the direction opposite to the reentry pulse. Ultimately, it collides with the reentry pulse, leading to complete annihilation. If an ATP stimulus is delivered to quiescent tissue, it creates two counter propagating pulses and the reentry is not terminated. The description above assumes, however, that the medium is homogeneous.

The situation is more complex in two dimensions. In this case, an anatomical reentry is a spiral wave rotating around an obstacle. To terminate the reentry, it is necessary to create a wave that can annihilate the rotating wave. This is more difficult than in the one-dimensional scenario because, in the two-dimensional scenario, the wave is characterized not only by its sense of rotation, but also by a complete wave form. As in the one-dimensional situation, an ATP stimulus must be delivered inside the vulnerable window, but this condition alone is not sufficient. When the ATP electrode is situated far from the obstacle, the nucleated wave has a free end that is separated from the obstacle. Thus, ATP is only successful when the free end merges with the obstacle. Only then, two counter propagating waves annihilate and the anatomical reentry is terminated. This is possible only if the distance from the free end of the nucleated wave to the obstacle is smaller than a critical distance (of the order of the core size of a free vortex, from several cm to several mm in cardiac muscle).

On the other hand, when a stimulating electrode is placed far from the obstacle, then ATP does not terminate the reentry, but instead creates a free reentry in addition to the anatomical one. When ATP is not successful, it is usually followed by conventional defibrillation techniques, which have unwanted side effects. These effects may include: (1) transient ectopy, tachycardia or induction of ventricular fibrillation; (2) depression of electrical and mechanical functions; (3) bradycardia, complete heart block and increased pacing thresholds; (4) atrial and ventricular mechanical dysfunction (stunning), which is directly related to the strength of shocks; (5) significant elevation of Troponin I serum level in patients after spontaneous cardioverter defibrillator shocks; (6) decrease of the myocardial lactate extraction rate by mitochondria. In addition to physical damage to the heart muscle, defibrillation therapy is also associated with psychological side effects. High energy discharge of a defibrillator in a conscious patient is painful and extremely unpleasant. Recent clinical studies have demonstrated that ICD patients have a significantly higher incidence of anxiety, depression, and panic disorders than do the general population.

What is needed, therefore, is a method for terminating an anatomical reentry using an energy level lower than that of conventional defibrillation techniques. Further, it is desirable that such a method be effective even when the precise location of the reentry is unknown.

SUMMARY OF THE INVENTION

The present invention provides a method for extinguishing a cardiac arrhythmia by destructive interference of the passing of the reentry wave tip of an anatomical reentry through a depolarized region created by a relatively low voltage electric field in such a way as to effectively unpin the anatomical reentry. Preferably, the relatively low voltage electric field is generated by electrical unpinning shocks that are intended to be lower than a lower limit of vulnerability as established, for example, by a defibrillation threshold test. By understanding the physics of the electric field distribution between cardiac cells, the method permits the delivery of an electric field sufficient to unpin the core of the anatomical reentry, whether the precise or estimated location of the reentry is known or unknown and without the risk of inducting ventricular fibrillation. A number of embodiments for performing the method are disclosed.

The method of terminating anatomical reentrant tachyarrhythmias utilizes one or more low voltage unpinning shocks that are applied in such a way as to effectively unpin the reentry from its core that is stabilized at a myocardial heterogeneity such as a scar. Preferably, the unpinning shocks are sub-threshold low voltage shock(s) that generate an electric field that is approximately 5-10 times weaker than the electric field generated by a conventional defibrillation shock and preferably below an expected lower limit of vulnerability for a defibrillation threshold, while greater than conventional pacing or ATP pulses.

In one embodiment, this method utilizes a theory of virtual electrode polarization (VEP) that predicts the creation of hyperpolarized and depolarized regions on opposite sides of a functional or anatomical heterogeneity in response to an applied external electric field. The areas of depolarization can give rise to secondary sources of excitation. When shock application is properly timed relative to the reentry wave tip, these secondary sources are induced at the anatomical heterogeneity that serves as the core of reentry. Therefore, VEP can be used to destabilize and unpin a reentrant arrhythmia.

In a preferred embodiment of the present invention, anti-repinning (ARP) pulses are applied after the low voltage unpinning shocks to avoid immediate repinning of the anatomical reentry at its core and facilitate complete termination of the now unpinned reentry that has been transformed into a functional reentry. Conventional ATP pulses have difficulties terminating anatomical reentry when the pacing site is located at a distance from the reentry core. However, there are no such difficulties associated with ATP termination of a functional reentry. Therefore, once the reentry is unpinned from its anatomical core, ARP pulses in accordance with the present invention can be effectively administered for terminating these now functional reentries and preventing their reattachment to a new core.

In this preferred embodiment, the ARP pulses are applied for purposes of completing the termination of the reentries, not for purposes of regulating a cardiac heart rate. In this way, the ARP pulses as contemplated by the preferred embodiment of the present invention are significantly different that the few prior art approaches such as U.S. Pat. Nos. 4,384,585, 5,265,600, 5,676,687 and 6,157,859, that have attempted to use conventional pacing pulses for the purpose of regulating heart rate, especially after atrial cardioversion.

In one embodiment of the present invention, the method is accomplished by establishing a termination window (TW), applying one or more low energy unpinning pulses in the target TW to unpin a rotating wave associated with one or more anatomical reentries causing the ventricular tachyarrhythmia, and immediately following the low energy unpinning shocks with anti-repinning (ARP) pulses to exterminate any unpinned, functional reentries. In this embodiment, there is no need to attempt to verify successful conversion of the arrhythmia prior to deliver of the ARP pulses because the process of terminating the arrhythmia in accordance with this embodiment of the present invention is essentially a multiple stage process of first unpinning anatomical reentries and then extinguishing all functional reentries, including any unpinned and now functional reentries that were originally anatomical reentries. In one variation of this embodiment, a dominant frequency (DF) for a ventricular tachyarrhythmia is determined based on ECG data. The DF is then used to establish the target TW. In an exemplary embodiment, the period defined by 1/DF would be divided by a small number, such as three, to establish the termination window.

In some embodiments of the present invention, the method is accomplished by identifying an estimated location of the anatomical reentry and using the information on the location of the anatomical reentry and the location and configuration of an electrode arrangement to estimate propagation delays for purposes of timing delivery of the unpinning shock(s). Unlike earlier attempts at cardioversion, the present invention does not time delivery of the unpinning shocks in relation to some aspect of the QRS complex of the cardiac signal of a patient. Instead, these embodiments of the present invention time delivery of the unpinning shocks based on measured, estimated or empirical data of the delay for a given relationship between the locations of the particular electrode configuration and the location of the heterogeneity associated with the anatomical reentry. Alternatively, other embodiments of the present invention utilize initially random timing of delivery of the unpinning shocks that is preferably coupled with empirical heuristic refinement of the timing and patterns of delivery of unpinning shocks.

One embodiment of the estimated timing approach utilizes rough approximation of the estimated location of the anatomical reentry by evaluating ECG signals received from at least three pairs of sensing electrodes in order to triangulate the estimated location in 3D space. This embodiment can be implemented in either a real time configuration or in an embodiment in which the estimated location of likely anatomical reentries is determined, for example, during defibrillation threshold testing during an implantation procedure for the electrode arrangement and/or an implantable cardiac stimulation device, such as an implantable cardioverter defibrillator (ICD). In this later embodiment, the triangulation of the estimated location of one or more existing heterogeneities in the heart of a patient that may be likely to be the source of future anatomical reentries is based on the identification of those existing heterogeneities during defibrillation threshold (DFT) testing.

Unlike existing approaches to DFT testing, one embodiment of the present invention utilizes the DFT testing process that is part of a conventional implantation procedure for a cardiac stimulation device to determine an upper limit of vulnerability (ULV) that will be used to establish a safety margin for the defibrillation therapy to be delivered by the implantable device. Instead of determining just a ULV for a given patient, this embodiment of the present invention also determines a lower limit of vulnerability (LLV) below which electrical shocks from the electrode arrangement for the given implantable device will not induce fibrillation. This LLV is the utilized in a preferred embodiment as an upper bound for the sub-threshold, low voltage shocks that are utilized in accordance with the method of the present invention to effectively unpin anatomical reentries. Alternatively, the LLV may be established based on empirical or statistical data for similarly situated patients.

Another embodiment uses electrocardiographic imaging (ECGI) to non-invasively construct a more detailed representation of electrical activity of the heart for purposes of identifying heterogeneities that are likely to be responsible for anatomical reentries. ECGI systems can be used to solve the so-called "Inverse" problem of figuring out how to predict a source of an electric field based on measurements of that field made at a distance. One such ECGI system is described in Ramanathan, C. et al. "Noninvasive electrocardiographic imaging for cardiac electrophysiology and arrhythmia," *Nature Medicine,* 10.1038/nm1011, March 2004, a copy of which is attached and the disclosure of which is hereby incorporated herein by reference. Such an ECGI system could be implemented either during DFT or, in the case of external defibrillation, for example, in real time by an appropriate electrode configuration.

In this embodiment, during the arrhythmia, with no shock delivered, two measurements are performed from the constructed map (i) rotation phase phi of the reentry tip, and (ii) position of the reentry core. From these measurements, the following values are calculated: (i) the direction $\hat{E}$ of the electric field near the core, and (ii) the rotation phase $\hat{phi}$ of the reentry tip with respect to the direction E^. An unpinning shock in accordance with the present invention is then synchronized with event phy^=0. The shock is delivered at time t=t(phy^=0)+APD, where APD is the action potential duration determined from an ECG record. This same technique can be utilized for finding estimated locations of the secondary or "virtual" electrodes associated with the heterogeneities.

In another embodiment, the estimated location of the anatomical reentry causing a cardiac arrhythmia could be determined in real time based on signal and morphology analysis of ECG signals from multiple sensing electrode configurations, such as RV-RA electrode vs. RV-can vs. RA-can for purposes of triangulating the estimated location in 3D space.

In other embodiments of the present invention, no attempt is made to identify an estimated location of the anatomical reentry. In these embodiments, the method is implemented by delivering sub-threshold shocks that have a high probability of accomplishing the objective of unpinning the anatomical reentry without knowing the location of the anatomical reentry.

In one embodiment, the method is accomplished by detecting and storing the waveform of the electrograms (EG) recorded from the patient's heart, then determining the maximum negative derivative of the recorded waveform. A set of threshold values is then calculated for the waveform, while the negative derivative of the waveform is continuously calculated. When the negative derivative exceeds a third threshold value, a timer is started. When the time on the timer exceeds the patient-specific individually adjusted delay, a reentry termination shock is delivered to the patient's heart. Time of delivery of a sub-threshold shock is chosen so that the virtual electrode polarization (VEP) would be created at the anatomical obstacle around which the anatomical reentry rotates, at the descending phase of AP of the reentrant wave.

In another embodiment, multiple unpinning shocks are utilized to present alternative wave fronts to the anatomical reentry in order to increase the likelihood of destructively interfering with the wave tip. One such embodiment utilizes multiple (e.g., 3-4) unpinning pulses delivered over a TW period of 100-150 ms, where all of the pulses are delivered through the same electrode path. Another such embodiment utilizes multiple unpinning pulses that are delivered over a short period, but are delivered over different electrode paths so as to produce the equivalent of a vector rotating field to the anatomical reentry.

In another embodiment, the process of empirically determining a best-fit timing for delivery of the unpinning shocks is accomplished by an adaptive routine implemented in an implantable device, for example. In this embodiment a low energy termination window (TW) is defined to be approximately equal to about $1/5^{th}$ of the rotation period of the anatomical reentry. During a period of several second necessary to charge the high voltage capacitor to deliver a defibrillation shock, the method of the present invention is accomplished by iteratively having the device deliver an unpinning shock followed by ARP timed to a TW that is set to a delay of T/5 from the indication of the anatomical reentry in the ECG data. After a period of about a second, the ECG data is analyzed to determine if the arrhythmia has been converted. If so, then the device stores the time delay and utilizes this time delay as the initial time delay to attempt for any subsequent arrhythmia episodes. If the arrhythmia has not been converted, then the delay is set to a period of 2 T/5 from the indication of the anatomical reentry in the ECG data and the process of delivering the unpinning shock followed by ARP is repeated. The entire process is repeated if the previous delay period is unsuccessful until either all possible TW's have been attempted, or until the capacitor has been fully charged for delivery of a high voltage defibrillation shock. In subsequent episodes, the device would use the delay for TW that empirically resulted in the best fit for the last successfully converted cardiac arrhythmia. In one variation of this embodiment, multiple successful delays would be stored by the device and a heuristic learning algorithm and/or predictive algorithm would be used to determine an order of attempting the multiple successful delays for attempting to convert a new cardiac arrhythmia using an unpinning shock that is, preferably, followed by ARP.

In one alternative embodiment of the present method, the method also includes the step of determining whether the unpinning shock was delivered within a pre-set safety time period. If the unpinning shock was not delivered within a pre-set safety time period, a defibrillation shock is delivered at the time of expiration of the safety time period.

In another alternative embodiment of the present method, the method also includes the step of determining whether the anatomical reentry was terminated. If the reentry was not terminated, a defibrillation shock is delivered at the time of expiration of the safety time period.

BRIEF DESCRIPTION OF THE DRAWINGS

FIG. 2 depicts the basic mechanism of unpinning an anatomical reentry. The depiction utilizes the FitzHugh and BR models.

FIG. 12a shows typical confocal microscopy image showing predominately phosphorylated Cx43 (red) on the superfused surface of the tissue and predominately unphosphorylated Cx43 (green) in the mid-myocardium.

FIG. 12b shows signal intensities for phosphorylated and unphosphorylated Cx43 signals from the preparation pictured in FIG. 12a. These signals were averaged across a 1.26 mm section of tissue at increasing distances from the superfused surface of the tissue.

FIG. 12c shows a surface plot of signal intensities from the preparation pictured in FIG. 12a.

FIG. 12d shows mean signal intensities from 3 experimental animals.

FIG. 13a shows an activation map for pacing at a constant interval of 300 ms from location indicated with a star. Black arrow pointing to crowded isochrones indicates an area of slow conduction.

FIG. 13b shows a preparation photograph overlapped with the trajectory of points of phase singularity indicating the cores of two different stable reentries whose isochronal maps are shown in FIGS. 13c-13d.

FIG. 13c shows an isochronal map for a stable reentry rotating counterclockwise with 10 ms isochrones. Trajectory of points of phase singularity is shown with a yellow line. The core of this reentry corresponds to the area of slow conduction in FIG. 13a.

FIG. 13d shows an isochronal map for a stable reentry rotating clockwise with 10 ms isochrones. Trajectory of points of phase singularity is shown with a cyan line.

FIG. 13e shows optical traces recorded from reentry in FIG. 13d.

FIG. 16a is a steady-state activation map of reentry which uses a 3D trabecula in the reentry path of an isthmus mechanism of termination. Isochrones are 10 ms apart.

FIG. 16b is a polar plot of successful and unsuccessful shocks applied throughout all phases of reentry.

FIG. 16c is an optical recording from location indicated with a cyan box in FIG. 16a.

FIG. 16d is a local ECG recording from surface of the preparation.

FIG. 19b is a series of images showing corresponding incidence and location of arrhythmias in a chronic infarction model in FIG. 19a.

DETAILED DESCRIPTION OF THE DRAWINGS

The present invention provides a method of unpinning and terminating an anatomical reentry, whether the precise or estimated location of the reentry is known or unknown. A background discussion of the mathematical and scientific basis underlying the monodomain and bidomain cell models which the present invention builds upon is presented, followed by a discussion of the present invention and some of the experimental data and results supporting the present invention.

Intracellular clefts in cardiac tissue are small areas—smaller than the cardiac cells themselves—resulting in complex electrical patterns. For a point injection of current, these clefts create a quadrupole distribution of membrane potential near an electrode. Near an obstacle, an electrical field creates a hexapole distribution superimposed over a dipole. This is valid also for an obstacle around which an anatomical reentry rotates.

Figure 1:
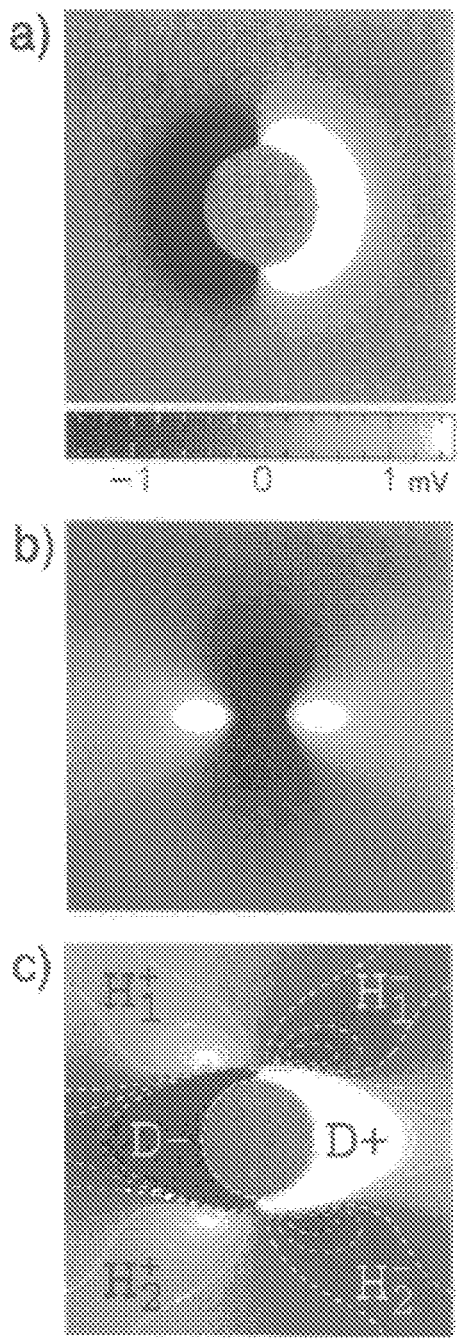
FIG. 1 depicts the dipole, quadrupole, and hexapole patterns induced by an electric field in the bidomain model of cardiac tissue.

Dipole, quadrupole, and hexapole patterns induced by an electric field in a bidomain model of cardiac tissue are shown in FIG. 1. FIG. 1(a) shows a dipole, FIG. 1(b) a quadrupole, and FIG. 1(c) a hexapole. FIG. 1(a) illustrates the result of an object 6 mm in diameter, with an anisotropy ratio a=1, E=0.2 V/cm. FIG. 1(b) illustrates the result of a point-based injection of current I=1.8 µA, a=10. FIG. 1(c) is the same object as in FIG. 1(a), where a=10. Contours are drawn at intervals of 0.4 mV. The bidomain model is used with the following values: $G_m=0.165$ mS/cm$^2$, $\sigma_{ex}=\sigma_{ey}=\sigma_{ix}=14.4$ mS/mm, $\sigma_{iy}=1.44$ mS/mm, $\beta=2000$ cm$^{-1}$.

The present invention focuses on how an electric field may be used to unpin an anatomical reentry in terms of how to unpin a rotating vortex. The minimal energy required for an electrical field that can accomplish the unpinning, as estimated theoretically, is ~100 times less than the energy traditionally used in defibrillation (FIG. 3; the energy is proportional to the electric field squared). In rabbit hearts experiments, the observed decrease of energy was on the scale 10-20 times as compared to conventional defibrillation. The following example demonstrates this.

Example

The model describes the extracellular potential, $\phi\Phi_e$, and the intracellular potential, $\phi\Phi_i$:

$$\nabla \cdot \sigma_i \nabla \phi_i = \beta \left[ C_m \frac{\partial}{\partial t}(\phi_i - \phi_e) + I_{ion} \right] - I_i, \quad (A)$$

$$\nabla \cdot \sigma_e \nabla \phi_e = -\beta \left[ C_m \frac{\partial}{\partial t}(\phi_i - \phi_e) + I_{ion} \right] - I_e. \quad (B)$$

where $\sigma_i$ and $\sigma_e$ are the conductivity tensors, and $I_i$ and $I_e$ are the externally injected currents in the intracellular and extracellular spaces, respectively. $\beta$ $\beta$ is the ratio of membrane surface area to tissue volume, $C_m$ is the membrane capacitance per unit area of the cell membrane, and $I_{ion}$ is the ionic current.

Equations (A) and (B) were used, along with ionic current ($I_{ion}$) as described by either the FitzHugh or BR model, or by the modifications of the BR model, above. A rotating waves pinned to a circular obstacle was numerically simulated, and the effects of an electric field for different timings and intensities were observed. For the relatively simple FitzHugh model, the entire set of possibilities leading to unpinning was explored. For the BR model, only situations relevant to cardiology (i.e. those with a weak electrical field) were explored.

Figure 2:
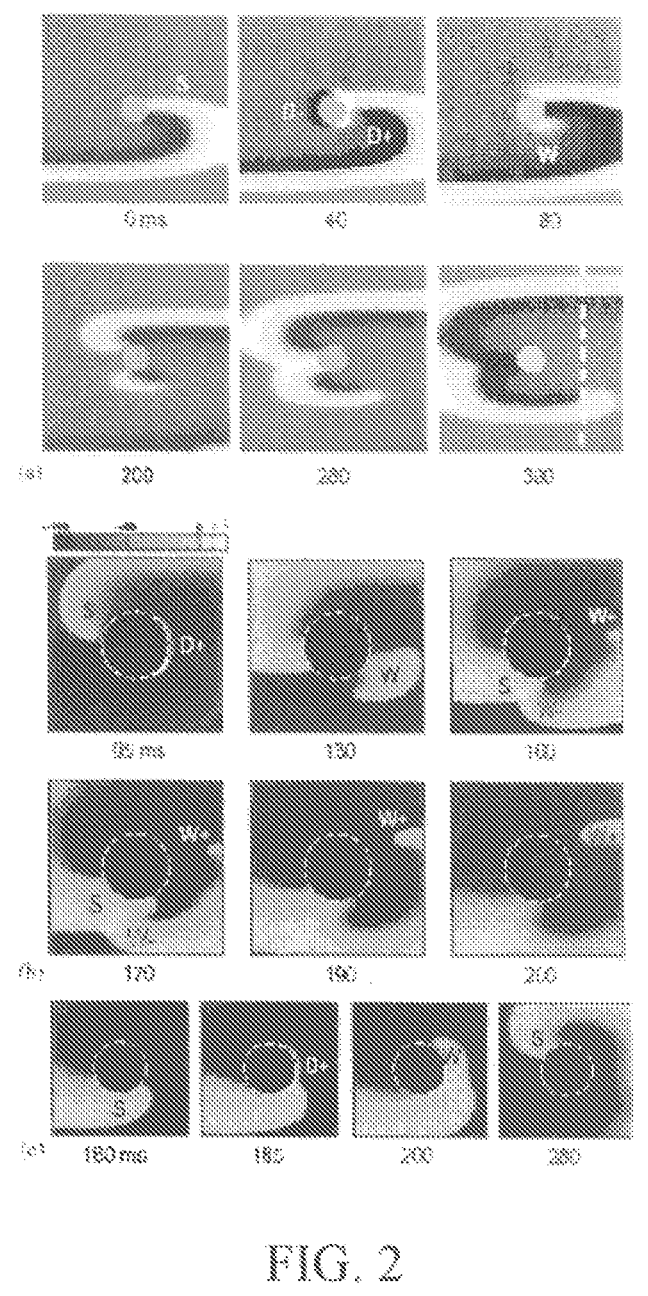

Rotating waves were numerically simulated in the full bidomain model with nonlinear ionic currents (using equations (A) and (B), above). The basic mechanism of unpinning can is described in FIG. 2. FIG. 2(a) illustrates the basic mechanism of unpinning. This portion of FIG. 2 relies on the FitzHugh model of a pinned spiral rotating wave at various time intervals as indicated in the figure. At time t=0 ms, a pinned spiral rotating wave S is shown. The wave is pinned to an obstacle, represented by the circle at the center of the wave. An electric pulse, 20 ms long, is applied from t=20 to 40 ms. At time t=40 ms, a dipole (D−, D+) is induced around the obstacle by an electric field having a strength of 0.52 V/cm. At t=80 ms, the positive part of the dipole D+ nucleates a new wave W. Near the obstacle, this waves propagates only clockwise (see t=200 ms, for example) due to the time of application of the pulse. At t=280 ms, the waves W and S collide. At t=360 ms, after annihilation of the colliding parts, the rotating wave is unpinned. If the medium is small enough (i.e. the boundary is located at the dashed line shown in FIG. 2(a)), then the reentry is terminated as shown at t=360 ms.

It is important to note that the wave W with the desired properties can be created only with proper timing of the electric pulse. Similar to ATP, if the pulse is delivered earlier it fits inside the restoration part of the propagating wave (i.e. inside the refractory tail), and no new wave will be nucleated. If the pulse is delivered much later, it will nucleate two counter propagating waves. The correct interval of stimulation (referred to as the termination window, VW, as noted above) is determined by the condition that the image of the nucleated wave W in the phase space should contain the Maxwell point inside. A more evident interpretation is: the nucleated wave W can propagate only in one direction if a part of its boundary has positive velocity (becoming a front of the wave) and another part has a negative velocity (becoming the tail of a wave). This condition sets both the time and voltage limits of the unpinning window.

FIG. 2(b) relies on the modified BR model (BR$_d$). Again, a model of a pinned spiral rotating wave at various time intervals is shown. At time t=95 ms, the D+ component of the dipole D−, D+ is induced around the obstacle (indicated by the circle at the center of the rotating wave) using an electric field of strength 0.5 V/cm. At t=130 ms, a new wave W is created by D+. Near the obstacle, this wave, denoted W−, propagates only clockwise. In this model, the wave W− does not contact the obstacle. At t=160 ms, the waves W− and S collide. A small piece of the pinned spiral wave S is not unpinned, but it decays. At t=200 ms, after annihilation of W− and S, the rotating wave rotates freely. The asymmetry of the nucleated wave W (which propagates only in clockwise direction) requires proper timing of the electric pulse, just at the tail of wave S. Without proper timing, the nucleated wave W either propagates in both directions, as in FIG. 2(c), below, or completely vanishes.

FIG. 2(c) also relies on the modified BR model, (BR$_d$), and illustrates a failed unpinning. A pinned spiral wave is shown at t=180 ms. At t=185 ms, the depolarized region D+ is created by an electric pulse of 0.5 V/cm. At t=200 ms, D+ gives rise to a wave W, which collides with S. At t=240 ms, the wave S continues to rotate around the obstacle.

Figure 3:
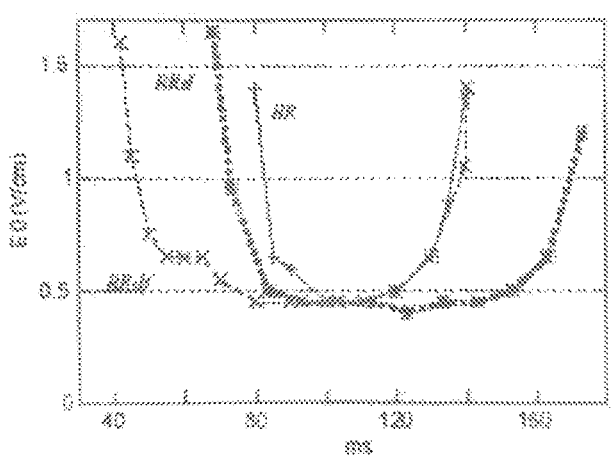
FIG. 3 is a graph illustrating the unpinning window for the BR model and two variations thereof.

From a practical standpoint, it is necessary to determine precisely how an electric field should be applied for an unpinning. That is, it is necessary to determine at what time the electric field should be applied, and at what strength. FIG. 3 shows the threshold electric field used to achieve unpinning, versus the time at which the electric field was applied. The results shown in FIG. 3 come from the three BR models described above (the original model and the two modified versions thereof). Importantly, unpinning is achieved in all three models using a low electric field (<0.5 V/cm). The date lines on the graph in FIG. 3 indicate the threshold amplitude of the electric pulse to achieve unpinning. A pulse of amplitude less than 0.5 V/cm can unpin for all of the versions of the ionic model. The BR$_d$ model is the most favorable for unpinning. The original BR model exhibits the smallest unpinning window, due to wave detachment.

Figure 4:
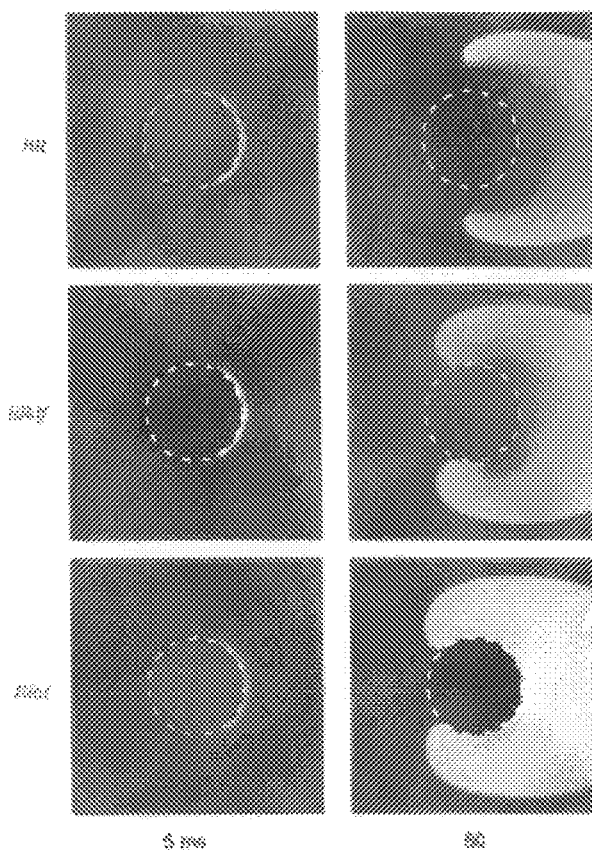
FIG. 4 illustrates the wave detachment observed with the standard BR model. The detachment is diminished with the modified BR models described herein.

By referring to FIG. 3, it can be seen why the modified models BR$_d$ and BR$_{df}$ were introduced above. As noted, the BR model has a smaller unpinning window than the modified models. This is due to an unexpected phenomenon, illustrated in FIG. 4. The figure shows that the wave nucleated by the electric field appears unpinned from the obstacle, although the rotating wave is pinned to it. This is due to the smaller size of the nucleated wave. The BR$_d$ and BR$_{df}$ models eliminate this phenomenon.

The basic unpinning mechanism is the same for both the FitzHugh and BR models given a low electric field (~0.5 V/cm). An analysis for unpinning with a larger voltage (>2 V/cm) appears below. This analysis utilizes the simpler FitzHugh model.

Figure 5:
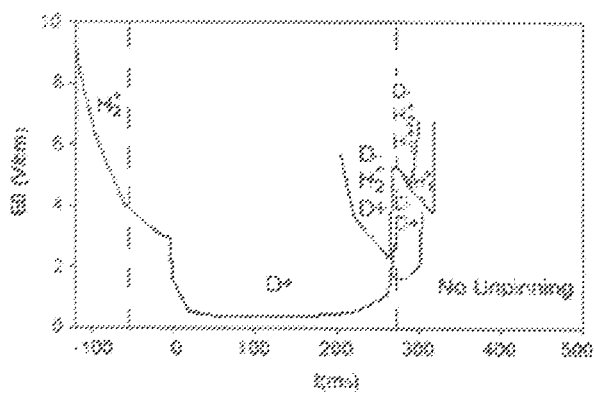
FIG. 5 is a graph illustrating different unpinning mechanisms observed for higher values of pulse intensity.

Extensive numerical investigation provides unpinning thresholds as a function of the time of the pulse. The results are given in graph form in FIG. 5. As the graph indicates, new scenarios appear relative to the low electric field results provided in FIG. 3, above. These new scenarios involve components of the potential, $H_{1,2}^+$, and/or the hyperpolarized regions of the dipole (D−). In the curves shown in FIG. 5, these scenarios are characterized by the lobe of the membrane potential distribution that interacts with the spiral wave.

Figure 6:
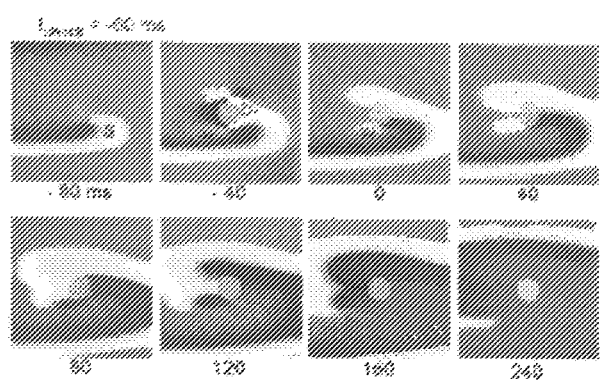
FIG. 6 illustrates an unpinning mechanism at larger voltage levels.

The unpinning scenario is shown in FIG. 6. The pinned wave S is shown at t=−80 ms. An electric shock of 4.5 V/cm is applied at t=−60 ms. At t=−40 ms, the depolarizing part of the dipole coincides with the rotating wave. Both the dipole and the hexapole are seen. At t=0 ms, a new wave W is created by the hexapole component $H_2+$. The waves created by $H_1+$ and by D+ merge with S. The wave W, propagating clockwise at t=40 ms, collides with the original rotating wave at t=80 ms. Annihilation of the colliding parts occurs from t=120 ms to 160 ms, and the wave is unpinned at t=240 ms.

In the heart, fibers are oriented at various angles. These various angles θ$_1$ (equations (J) and (K), above) will contribute to the unpinning. This can be understood by the analysis below. The electronic constant perpendicular to the fibers is smaller than parallel to them. For large obstacles (radius R>>λ), the maximum potential at the obstacle depends approximately linearly on the electronic constant λ. Linear approximation of the exact solution gives:

$$V_m^0(r=R, \theta=0) \approx \lambda\left(1 - \frac{\lambda}{2R}\right)E_0 \quad (R \gg \lambda) \tag{N}$$

When the electric field is rotated by 90°, $\lambda_y$ instead of $\lambda_x$ is used in the equation. As a result, the electric field will have a smaller effect when applied along y than along x, since the electronic constant is smaller:

$$\lambda_y = \sqrt{\frac{2}{1+a}}\,\lambda_x$$

where $a=\sigma_{i,x}/\sigma_{i,y}>1$ is the anisotropy ratio. The threshold of excitation, and of unpinning, is thus larger when the field is applied parallel to y.

Figure 7:
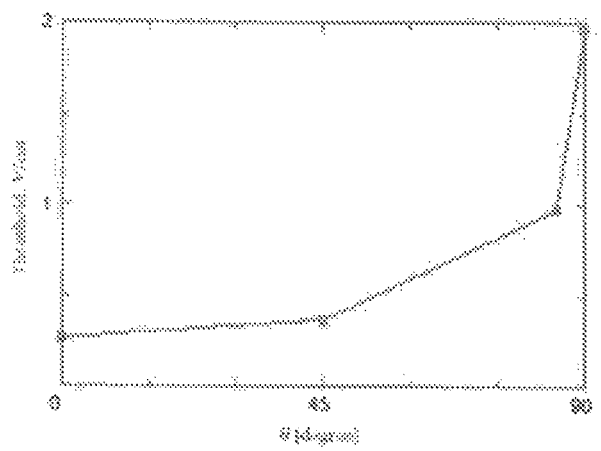
FIG. 7 is a graph illustrating the dependence of the unpinning threshold electric field on the angle of application of the current with respect to cardiac fibers.

More quantitatively, the perturbation analysis allows justification of the increased unpinning threshold. The transversal case $\theta_f=90°$ can be deduced from the parallel case by interchanging $\epsilon$ by $-\epsilon$ in the equation describing the intracellular tensor, above. Thus, dipolar and hexapolar corrections of the depolarized region have the opposite sign. This causes the unpinning threshold to become larger. The dependence of the unpinning threshold on the fiber direction is shown in FIG. 7. As can be seen, the threshold value remains low for almost all angles.

The termination threshold is also dependent on the size of the obstacle to which the rotating wave is pinned. For large obstacles (radius $R\gg\lambda\lambda$), the maximum potential at the obstacle depends approximately linearly on the electronic constant $\lambda\lambda$:

$$V_m^0(r=R, \theta=0) \approx \lambda\left(1 - \frac{\lambda}{2R}\right)E_0 \quad (R \gg \lambda)$$

Very small obstacles (~1 mm) are not capable of pinning rotating waves. In this situation, equation (N) is approximately valid because for typical cardiac tissue, $\lambda\lambda\sim1$ mm. Hence, the dependence of the depolarization on the obstacle size is weak for obstacle sizes that support rotating waves. The unpinning window, however, is modified.

Figure 8:
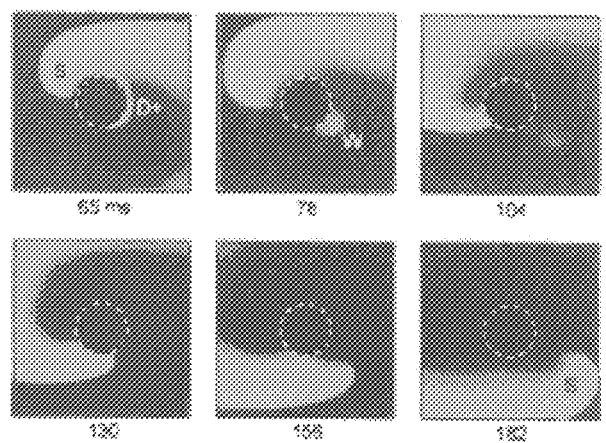
FIG. 8 depicts an unpinning scenario observed with small obstacles.

For obstacles not much larger than the limiting size to sustain a rotating wave, a new unpinning mechanism arises. This mechanism is shown in FIG. 8. At t=65 ms, D+ is induced by an electric field of strength 0.85 V/cm. When the electric field nucleates a wave W (t=78 ms) in the partially refractory region, it propagates away from the obstacle, as seen at t=104 ms, and decays (t=130 ms). The pinned wave meets the refractory tail of W and unpins at t=156 ms to 182 ms. Thus, for a small obstacle, the unpinning window becomes smaller in time but larger in phase units. For intermediate obstacles, the wave detachment may decrease the unpinning window as occurs for the original BR model. Finally, for large enough obstacles, all models have a low unpinning threshold and the same unpinning mechanism operating at this low electric field.

Figure 9:
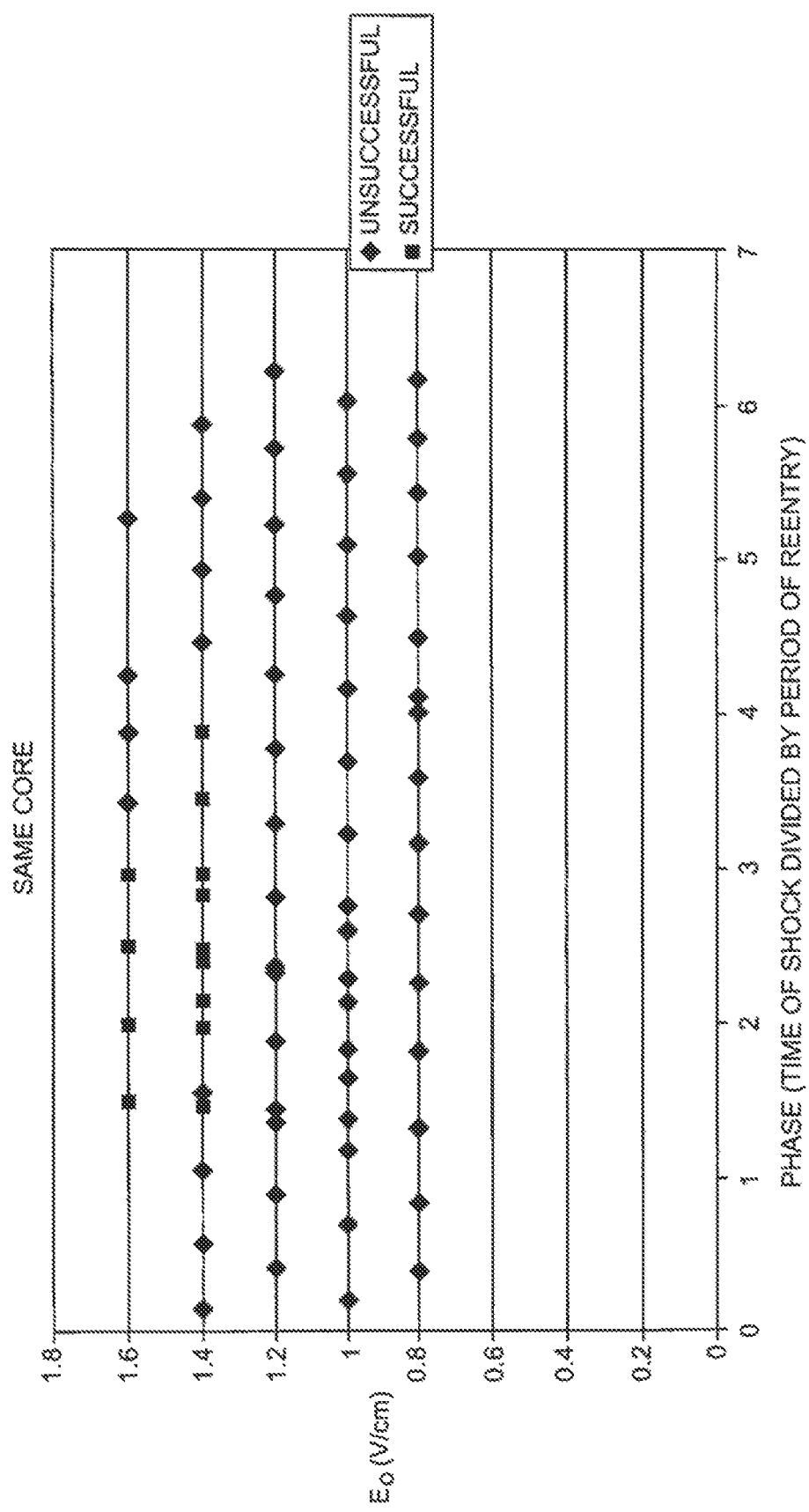
FIG. 9 is a graph showing the threshold of unpinning and termination of tachycardia in an isolated superfused right ventricular preparation from rabbit heart.

FIG. 9 is a graph showing the threshold of unpinning and termination of tachycardia in an isolated superfused right ventricular preparation from rabbit heart. Shock strength is shown in V/cm. Timing of the shock application is shown in radians, assuming that the period of tachycardia is 6.28 radians (two pi).

Figure 10:
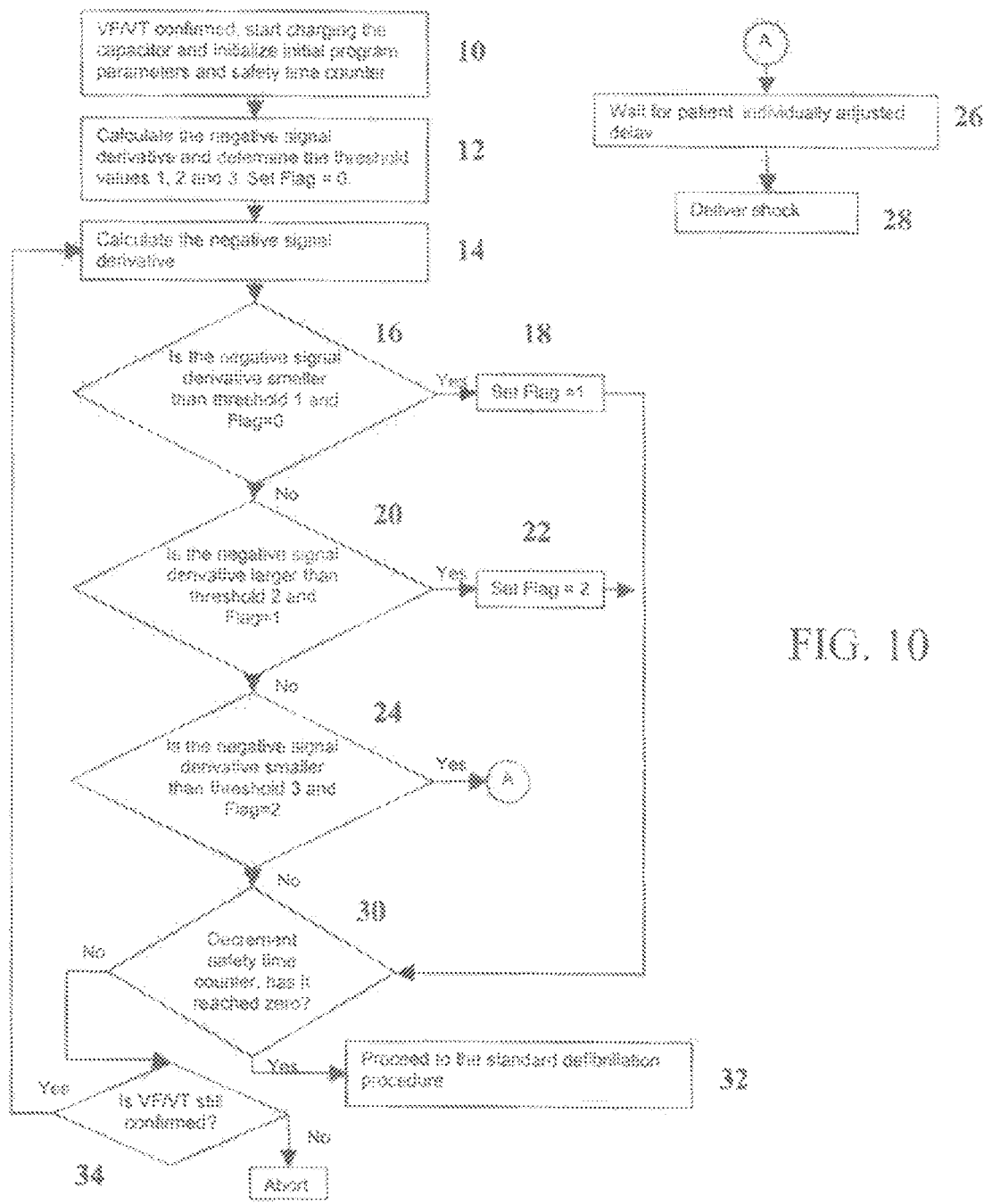
FIG. 10 is a flow diagram illustrating the one embodiment of the method of the present invention.

FIG. 10 provides a flow diagram illustrating one embodiment of the method of the present invention. Each of the steps in the method has been assigned a number in the drawing for the sake of clarity. Beginning, then, at the numeral 10, the VF/VT of the patient is confirmed and a high-voltage capacitor is charged. The initial program parameters and safety time counter are also initialized. Next, the negative signal derivative is calculated and the threshold values 1, 2 and 3 are determined. In addition, a flag is set to zero (12). The negative signal derivative is calculated once again (14). Then, a determination is made as to whether the negative signal derivative is smaller than threshold 1 and whether the flag is still set to zero (16). If the answer to both of these determinations is 'yes,' then the flag is set to 1 (18) and the method proceeds to the step indicated by the numeral 30. If the answer to either determination is 'no,' the method proceeds to the step indicated by the numeral 20. If the method has proceeded to the step indicated by the numeral 20, a determination is made as to whether the negative signal derivative is larger than threshold 2 and whether the flag is set to 1. If the answer to both determinations is 'yes,' then the flag is set to 2 (22) and the method proceeds to the step indicated by the numeral 30. If the answer to either determination is 'no,' then the method proceeds to the step indicated by the numeral 24. If the method has proceeded to the step indicated by the numeral 24, a determination is made as to whether the negative signal derivative is smaller than threshold 3 and whether the flag is set to 2. If the answer to both of these determinations is 'yes,' then the method proceeds to the step indicated by the numeral 26. After waiting for the patient's individually adjusted delay (26), a shock is delivered to the patient's heart (28). If the answer to either determination in the step indicated by the numeral 24, above, is 'no,' then the method proceeds to the step indicated by the numeral 30. A determination is made as to whether the safety time counter has reached zero (30). If the safety time counter has reached zero, a standard defibrillation shock is delivered (32). If the safety time counter has not reached zero, the method proceeds to the step indicated by the numeral 34. A VF/VT confirmation is performed (34). If VF/VT is not confirmed, the method is aborted. If VF/VT is confirmed, the method returns to the step indicated by the numeral 14 and proceeds as above.

The above analysis demonstrates the present mechanism of unpinning spiral waves by using a small electric field. An electric field with energy at least two orders of magnitude smaller than a defibrillation shock is enough to unpin the rotating wave. Importantly, the precise location of the pinning center is not required. The effect is based on the distribution of membrane potential generated near an obstacle in the presence of an externally applied electric field.

This embodiment of the present invention provides a method for low voltage termination of an anatomical reentry in a patient heart. In order to accomplish the desired result, the electrical waveform for the patient is detected and stored. The maximum negative derivative of the electrical waveform for the patient is also recorded. Next, a set of threshold values for the waveform parameter is determined. The negative derivative of the electrical waveform is continuously calculated and compared to the set of threshold values. A termination shock is delivered by a suitable cardiac stimulation device, such as, for example, as device containing a high voltage capacitor. The shock is delivered to the patient's heart during a period reentry when the patient-specific individually adjusted delay is provided after the negative derivative exceeds the third threshold value.

If the shock was not delivered within the safety time period, a prescribed defibrillation shock can be delivered at the time of expiration of the safety time period. Alternatively, the prescribed defibrillation shock can be delivered at the expiration of the safety time period if it is determined that the reentry was not terminated by the initial shock to the patient heart, as described above.

Referring now to FIGS. 11-17, details of the study of one embodiment of the present invention will be described. The study was performed to experimentally validate the possibility and effectiveness of this new method in an in vitro acute model of the infarction border zone (BZ), which is known to provide the anatomical substrate for reentrant tachycardia due to nonuniform conduction caused by remodeling of the BZ. Isolated superfused preparations of the rabbit right ventricular free wall were used in this study. The endocardial surface of the ventricle was superfused as a model of the endocardial BZ. In this model, stable reentrant arrhythmias that were easily visualized using voltage sensitive dyes and fluorescent imaging techniques were obtained. These ventricular tachycardias (VT) were driven by a single "mother rotor" reentrant source. Using low voltage shocks, we investigated mechanisms of unpinning and termination of "mother rotor" reentry pinned to a myocardial heterogeneity.

The study conformed to the guidelines of the American Heart Association. Experiments were performed in vitro on hearts obtained from New Zealand White rabbits (n=14) of both sexes weighing between 2-3 kg. The general steps of the experimental procedure have been described previously in detail in Nikolski V, Efimov I. "Fluorescent imaging of a dual-pathway atrioventricular-nodal conduction system," Circ Res. 2001; 88:E23-E30. Briefly, the rabbit was anesthetized intravenously with 50 mg/kg sodium pentobarbital and 1000-2000 units heparin. Following a midsternal incision, the heart was removed and placed onto a Langendorff apparatus, where it was coronary perfused at 20 ml/min flow rate with warm (36° C.), oxygenated (95% $O_2$, 5% $CO_2$) modified Tyrode's solution of the following composition (in mmol/L): NaCl 128.2, $CaCl_2$ 1.3, KCl 4.7, $MgCl_2$ 1.05, $NaH_2PO_4$ 1.19, $NaHCO_3$ 20 and glucose 11.1. The excitation-contraction uncoupler 2,3-butanedione monoxime (BDM, 15 mM, Diacetyl Monoxime, Sigma, St. Louis Mo.) was added to the perfusate to eliminate motion artifacts in optical recording caused by muscle contraction. The heart was stained with voltage-sensitive dye di-4-ANEPPS (5 min, 1.3 μM). Following staining, the heart was immediately removed from the Langendorff apparatus and placed in a bath of ice cold Tyrode's solution. The right ventricular free wall was dissected, stretched and pinned epicardial side down onto silicon disk. The preparation was then placed in a temperature controlled bath (36° C.) with Tyrode's solution where it was superfused at a rate of 80 ml/min.

The optical mapping system used for voltage-sensitive fluorescent imaging as previously described in the general steps of the experimental procedure. Briefly, light produced by a 250 W quartz tungsten halogen lamp (Oriel) passed through a 520±45 nm excitation filter and illuminated the preparation. The fluorescence emitted from the preparation was long-pass filtered (>610 nm) and collected by a 16×16 photodiode array (C4675, Hamamatsu, Japan). The signal from the photodiode array was amplified and digitized at a rate of 1500 frames/sec.

Figure 11:
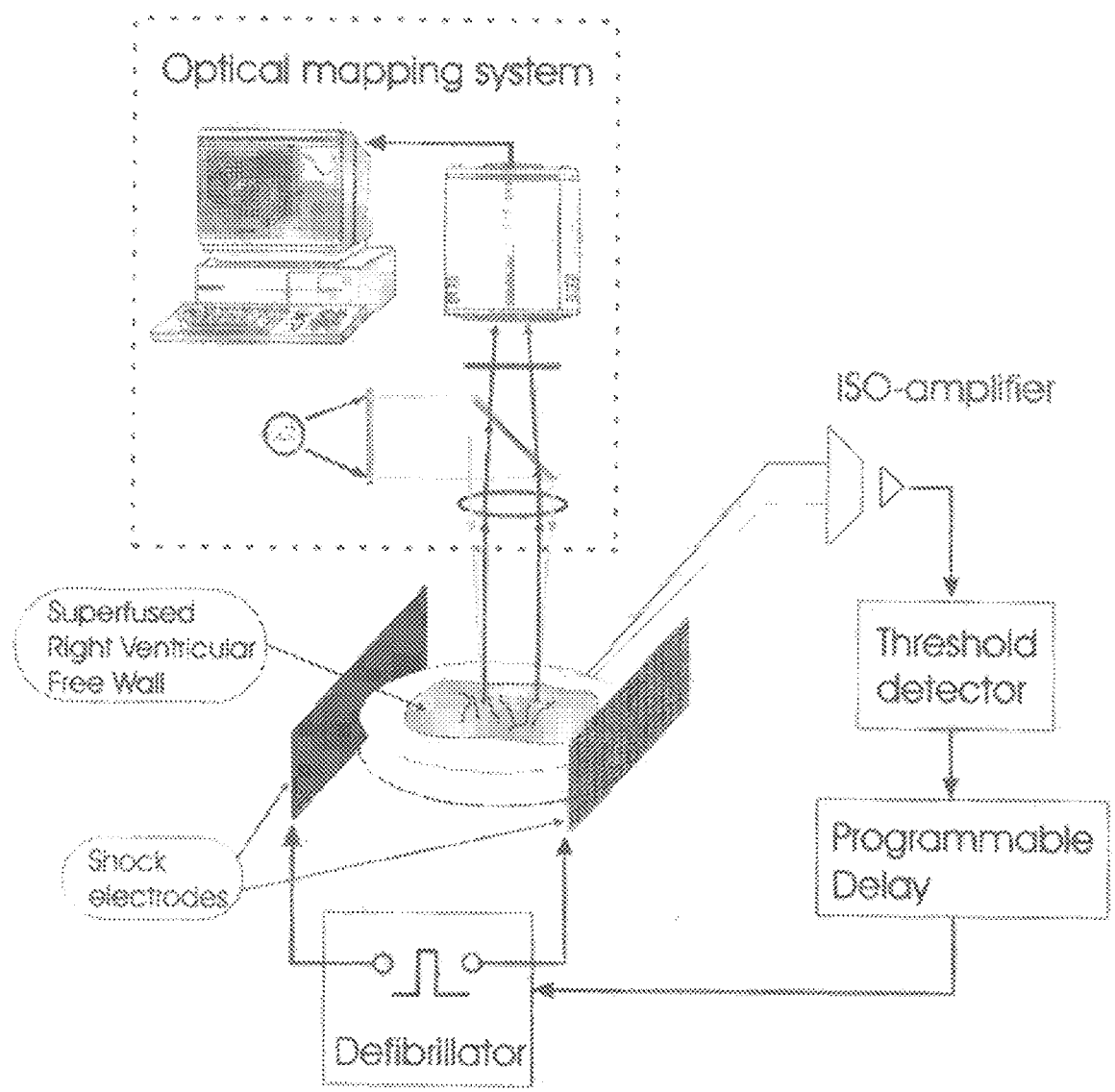
FIG. 11 is a block diagram of circuitry used to modulate time of shock application in accordance with one embodiment of the present invention.

A bipolar electrical recording from the preparation surface was used to trigger the shock application at the required phase of reentry. The signal was amplified with an isolation amplifier. A threshold detector determined the time of local activation and a shock was delivered across electrode meshes located in the bath after a programmable delay. FIG. 11 shows a block diagram of this setup. After amplification of the ECG signal, a threshold detector was used to mark the time of excitation. From this time of local activation, a shock was delivered with a specified delay. Field strength was calibrated with unipolar electrode recordings taken in the center of the chamber between the meshes. A Kepco 100V regulated power supply (BOP-100-4M) was used a power amplifier for delivering shocks, which were synthesized by a digital-to-analog controller integrated into a data acquisition system.

After a 15 min equilibration period, the field excitation threshold was determined. Stable reentry was then initiated by a burst pacing at an interval of 100-130 ms. Shocks consisting of 10 ms monophasic square pulses were applied at an initial field strength of 0.25 V/cm. The timing of shock application was varied throughout the entire period of reentry at 10 ms steps until the whole period of reentry was scanned. If the full period of reentry was scanned and the reentry did not terminate, the magnitude of the shocks was increased in 0.1 V/cm increments and scanning of the period was repeated. Once terminated, reentry was immediately reinitiated. If shocks were not applied, the stable reentry would last anywhere from 20 minutes to 1 hour (this was the longest time period we allowed the reentry to continue).

After 3 experiments, the preparation was embedded in Tissue-Tek® O.C.T. compound and frozen. The 16 μm transmural cryosections were mounted on poly-L-lysine coated glass slides. Immunohistochemistry was conducted as described previously. Briefly, double staining was performed with a commercially available anti-phosphorylated (Ser368) connexin 43 (Cx43) polyclonal antibody raised in rabbit (catalog no. AB3841, Chemicon) used at a dilution of 1:400 and with a commercially available anti-unphosphorylated (Ser368) Cx43 monoclonal antibody raised in mouse (catalog no. 13-8300, Zymed) used at a dilution of 1:200. Alexa fluor 488 goat anti-mouse $IgG_1$ (catalog no. A-21121, Molecular Probes) and Alexa fluor 555 goat anti-rabbit IgG (catalog no. A-21428, Molecular Probes) were used as secondary antibodies at dilutions of 1:1000. Confocal imaging was then performed using a Nikon C1/80i confocal microscope.

Microscopy images were analyzed by determining the means of the normalized phosphorylated Cx43 and unphosphorylated Cx43 signal intensities averaged over 1.26×0.080 $mm^2$ areas along and across the tissue surface. The depth of the surviving layer of tissue for each section was determined to be the distance at which the mean phosphorylated and unphosphorylated signal intensities intersected. The differences between the phosphorylated and unphosphorylated signal intensities were analyzed by one-way repeated measurements ANOVA.

Phase plane analysis was performed on reentry data to determine the location of the reentry core which is indicated by a point of phase singularity (PS). Specifically, the Bray-Wikswo method of pseudo-empirical mode decomposition (PEMD) along with the Hilbert transform was used to generate the phase plane data. To determine lines of block created by the reentry cores, the PS trajectories were also obtained by tracking the locations of PS throughout one or more periods of reentry. Activation maps were then created using two different methods. For paced data or reentry which included a three dimensional path (see FIGS. 16a-16d), activation maps were created by determining the local activation time (maximum of the first derivative) corresponding to each photodiode signal. For the reentry data, after phase-plane analysis was performed, isochronal maps were created by tracking the location of the wavefront in the phase plane throughout the entire period of reentry.

Rayleigh's test was used to determine if the phase of successful shock application was statistically different from a circular uniform distribution. The concentration and angular mean of successful shocks were also determined. Data are presented as mean±standard error of mean. P-values less than 0.05 were considered significant.

The preparations were superfused. Thus, it was expected that midmyocardium would be subjected to ischemia and cellular uncoupling due to dephosphorylation of Cx43.[45] Staining with anti-phosphorylated and anti-unphosphorylated Cx43 antibodies revealed that only a thin layer of tissue had phosphorylated Cx43 after 1-2 hours of superfusion, while the midmyocardium had only unphosphorylated Cx43.

Figures 12A, 12B, 12C, 12D:
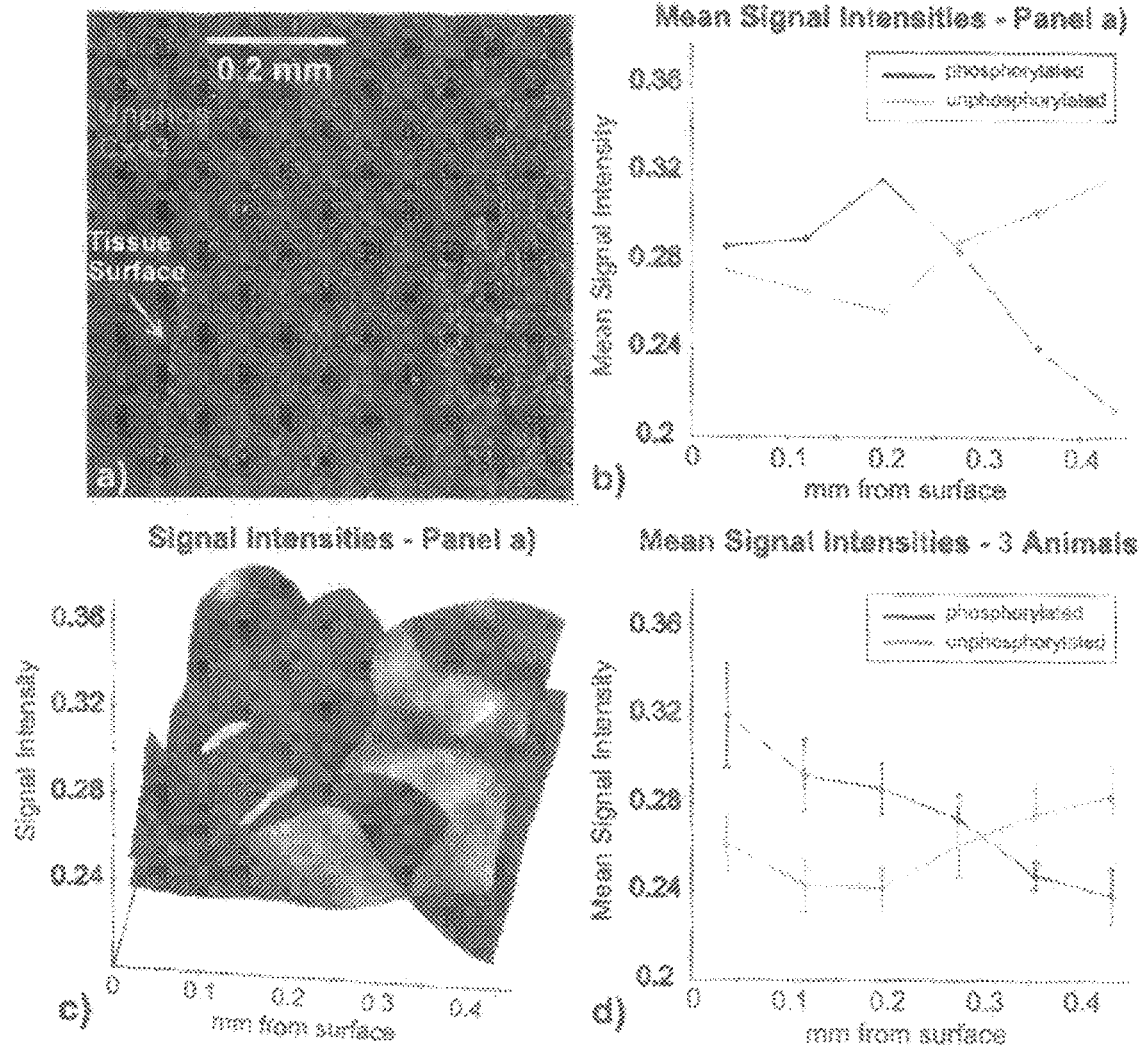

FIGS. 12a-12d show a summary of these results. A typical confocal microscopy image at 10× magnification is shown in FIG. 12a. The endocardial superfused surface of this preparation is the left edge of the tissue section. Phosphorylated Cx43 is shown in red, with the signal extending from the endocardial surface to approximately 0.30 mm into the tissue. Unphosphorylated Cx43 is shown in green which becomes visible at approximately 0.30 mm from the surface and extends to the edge of the photograph. The averaged normalized signal intensities (see Methods) for the preparation pictured in FIG. 12a are shown in FIG. 12b, again with phosphorylated Cx43 shown in red and unphosphorylated Cx43 shown in green. The depth of the surviving layer of tissue was determined to be the intersection of these two signals, and for this preparation was 0.299 mm. FIG. 12c shows a surface plot of the signals across the width of the tissue section pictured in FIG. 12a before the means were calculated. Combined results from 3 animals are shown in FIG. 12d. The phosphorylated and unphosphorylated signals were significantly different throughout the depth of the tissue (p=0.0036, one way repeated measurements ANOVA). The average depth of tissue at which phosphorylated Cx43 was of higher density as compared to unphosphorylated Cx43 was 0.38±0.10 mm.

In all studied preparations, the activation sequence during pacing and during reentrant tachycardia induced by burst stimulation was characterized. Interestingly, in all preparations it was observed that the arrhythmias were driven by a single reentrant circuit in accordance with the "mother-rotor" mechanism.

Figures 13A, 13B, 13C, 13D, 13E:
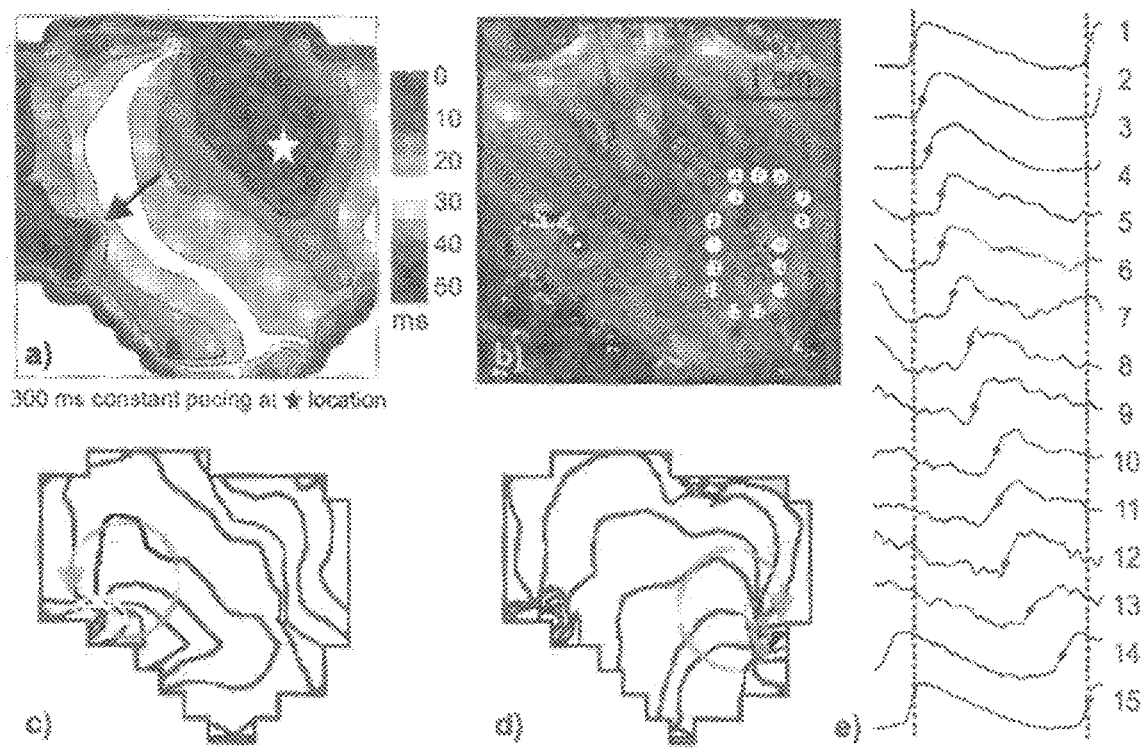

FIGS. 13a-13e illustrate typical results obtained from a single preparation for constant pacing and stable reentry. FIG. 13a shows a map of activation produced by constant pacing applied with a cycle length of 300 ms at the site indicated with a star. The black arrow is pointing to an area of crowded isochrones, indicative of slow conduction. A preparation photograph is shown in FIG. 13b along with the trajectories of PS obtained for two different stable reentries observed in this experiment, indicating the location of the core for each reentry. Numbers in FIG. 13b correspond to the location of each optical signal. The activation times (black circles) were determined by the maximum of the first derivative. White circle at trace 1 indicates activation for the next rotation of reentry. The isochronal maps for these reentries are shown in FIGS. 13c-13d, with the yellow core corresponding to the isochronal map in FIG. 13c and the cyan core corresponding to the isochronal map in FIG. 13d. The trajectories of PS are also shown on the isochronal maps in FIGS. 13c-13d. It is not surprising that the reentry core in FIG. 13c corresponds to the area of slow conduction observed during constant pacing illustrated in FIG. 13a, as this area of slow conduction is heterogeneous with respect to the surrounding tissue and provides the substrate to pin a reentrant arrhythmia. Several optical signals are shown in FIG. 13e illustrating the progression of activation around the reentry core illustrated in FIG. 13d. The locations of the recording sites for each of the optical signals are shown with corresponding numbers on FIG. 13b. The activation times determined for each signal as $(-dF/dt)_{max}$ (where F=fluorescence signal recording) are shown with black dots. The white circle in trace 1 indicates activation for the next rotation of reentry.

Figures 14A, 14B, 14C, 14D, 14E, 14F:
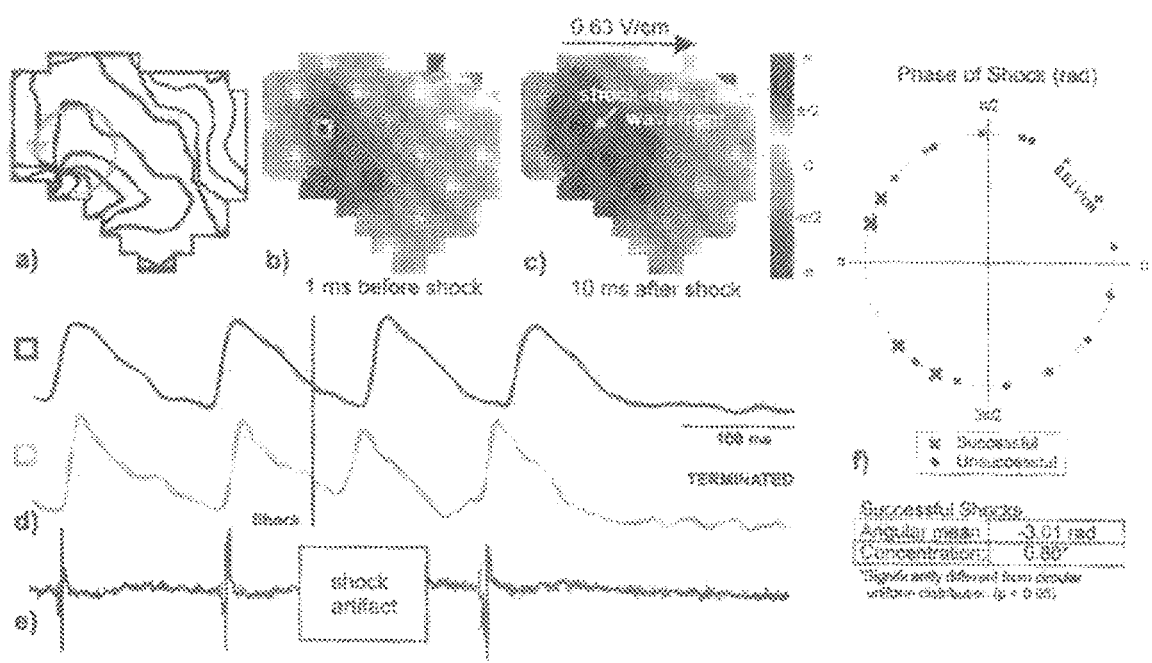
FIG. 14a shows a steady-state isochronal map with 10 ms isochrones.
FIG. 14b shows a phase-plane map 1 ms before shock application. White circle indicates location of the phase singularity.
FIG. 14c shows a phase-plane map 10 ms after shock application showing a new region of depolarization near the reentry core.
FIG. 14d shows optical traces from the locations indicated with corresponding colored boxes in FIG. 14b. Shock-induced depolarization can be observed in the cyan trace.
FIG. 14e shows local ECG recording from surface of the preparation.
FIG. 14f shows a polar plot of successful and unsuccessful shocks applied throughout all phases of reentry.

The first example of low-voltage termination of reentry presented here is similar to the mechanism predicted by bidomain simulations of the present invention in which a "secondary source" of excitation is created near the reentry core immediately after shock application, presumably due to the VEP mechanism at the heterogeneity serving as the reentry core. FIGS. 14a-14f illustrate this example. The isochronal map for stable reentry is shown in FIG. 14a, rotating counterclockwise with a period of 146.4 ms. FIG. 14b shows the phase plane and location of PS (white dot) 1 ms prior to shock application. A shock of 0.63 V/cm was then applied. Ten ms after shock application, a new shock-induced wavefront can be observed in the phase plane as indicated by the depolarized red region near the PS in FIG. 14c. Optical traces from the locations indicated with corresponding colored boxes in FIG. 14b are shown in FIG. 14d and the surface ECG recording is shown in FIG. 14e. The red optical trace appears unaffected by the shock, whereas shock-induced depolarization can be observed in the cyan optical trace. This new wave of depolarization then collided with the reentrant wavefront, unpinning it from the reentry core. The unpinned reentry then made two additional rotations with the core located far from the area of pinning before it reached the edge of the preparation and terminated. Each termination of this reentry proceeded in a similar manner, with the unpinned reentry making anywhere from 0-3 additional rotations before termination at the border of the preparation. A polar plot of successful and unsuccessful 0.63 V/cm shocks applied throughout all phases of reentry is shown in FIG. 14f. Successful shocks were clustered around the angular mean with a concentration of 0.80. Rayleigh's test found the distribution of successful shocks to be statistically different from a uniform circular distribution (p<0.05).

Interestingly, reentry in all preparations was highly reproducible. Although, the exact location of the mother rotor could be different from tachycardia induction to induction, it was always stationary.

Figures 15A, 15B, 15C, 15D, 15E, 15F:
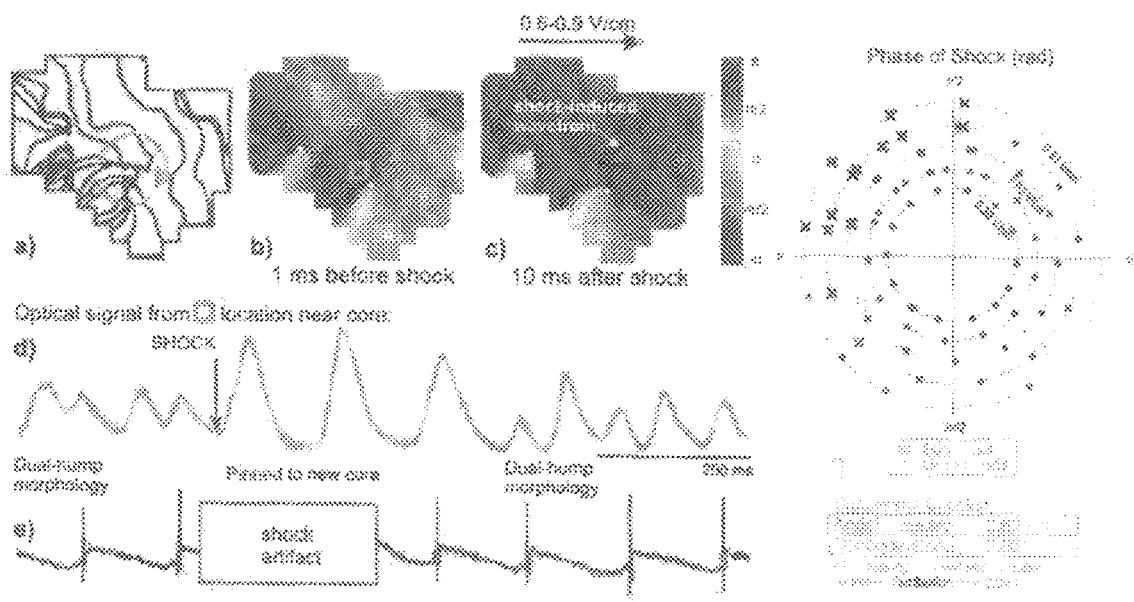
FIG. 15a is a steady-state isochronal map with 10 ms isochrones for unpinning of reentry by virtual-electrode induced excitation of the reentry core without termination.
FIG. 15b is a phase-plane map 1 ms before shock application. The phase singularity of the mother rotor is located in the center of the preparation.
FIG. 15c is a phase-plane map 10 ms after shock application showing a new region of depolarization near the reentry core.
FIG. 15d is an optical trace from a location near the reentry core indicated with a cyan box in FIG. 15b.
FIG. 15e is a local ECG recording from surface of the preparation.
FIG. 15f is a polar plot of successful and unsuccessful shocks applied throughout all phases of reentry.

The example of unpinning of reentry by virtual electrode-induced excitation of the reentry core without termination is similar to the previous example in that a shock-induced secondary source of excitation near the reentry core collided with and unpinned the reentry. However, in this case, the reentry did not proceed to the edge of the preparation and terminate. Instead, it pinned to a new location for several beats. After making 1-5 rotations around this new core, the reentry then repinned back to the original core, which apparently had stronger pinning force. The steady-state isochronal map for this reentry is shown rotating clockwise with a period of 131.0 ms in FIG. 15a. The phase-plane map 1 ms prior to shock application is shown in FIG. 15b. The PS of the mother rotor is indicated with a white dot in the center of the preparation. Additional PSs were present elsewhere in the preparation due to transient block of conduction, however full rotations were not maintained around these PSs. Ten ms after shock application, a new wavefront was created near the reentry core as indicated by the depolarized red region in FIG. 15c. Before shock application, a dual-hump morphology is observed which indicates the presence of a reentry core. After shock application, 3 full magnitude APs are recorded while the reentry is pinned to a new location. The reentry then spontaneously repinned to the original reentry core and the dual-hump morphology is again observed. This wavefront then collided with and unpinned the reentry. Although the reentry was unpinned, it immediately reattached to a new core, where it made several rotations before spontaneously moving back to the original reentry core. Unpinning of reentry was verified with optical signals recorded from locations near the original reentry core. One such signal is shown in FIG. 15d. This signal was taken from a location near the original reentry core indicated with a cyan box in FIG. 15b. Before shock application, a dual-hump morphology can be observed, indicating that this location is at the core of a reentrant arrhythmia. Immediately after shock application, the dual-hump morphology is no longer present and 3 full magnitude APs are recorded. The reentry then spontaneously repinned back to its original core and the dual-hump morphology can again be observed. The corresponding surface ECG recording is shown in FIG. 15e. FIG. 15f shows a polar plot of successful and unsuccessful shocks applied throughout all phases of reentry. Successful shocks were clustered around the angular mean with a concentration of 0.80. Rayleigh's test found the distribution of successful shocks to be statistically different from a uniform circular distribution (p<0.001). Such unpinning without termination was observed in 1 preparation out of 14.

Figures 16A, 16B, 16C, 16D:
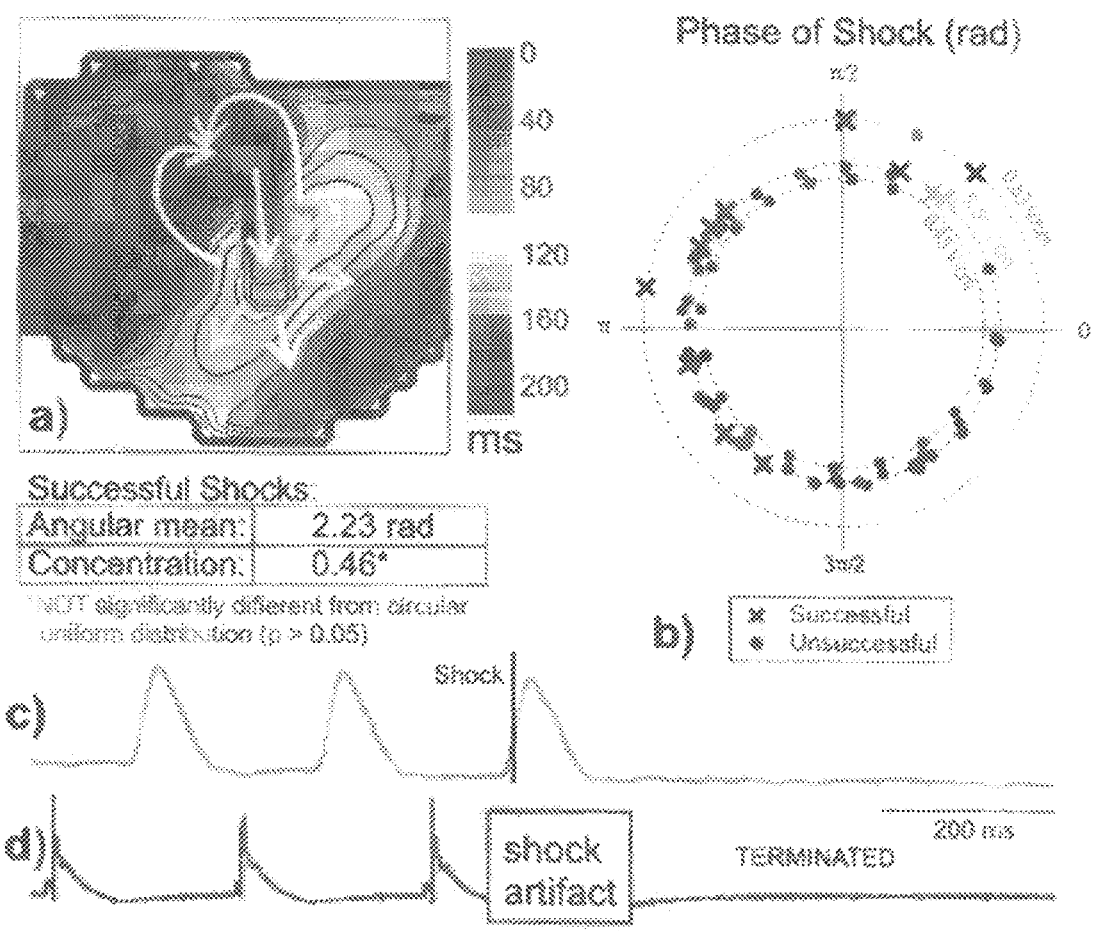

In 2 experimental preparations, reentry circuits were observed which included a narrow isthmus of tissue. In these cases, low-voltage termination was different than the previous examples. For these reentrant circuits, the timing of shock application was not as critical as it was for previous examples. Rather, termination was achieved at practically any phase of reentry. This mechanism occurred when the reentry was rotating near the edge of the preparation or when the reentrant path included a 3D trabecular structure as in the example presented here. The activation map for this reentry is shown in FIG. 16a, with the reentrant pathway indicated with yellow arrows. In the middle of the preparation, the pathway included a narrow trabecular structure. As can be observed in the polar plot of successful and unsuccessful shocks in FIG. 16b, termination of this arrhythmia had a threshold-like behavior. Successful shocks were found to have a very low concentration (0.46) around the angular mean which was not significantly different from a circular uniform distribution. Below 0.51 V/cm, termination could not be achieved at any phase of reentry. However, above this value, termination could be achieved over many phases of reentry. This observation was confirmed with Rayleigh's test which found the successful shocks to have a relatively low concentration (0.46) around the angular mean, which was not found to be statistically different from a uniform circular distribution (p>0.05). It is believed that this phenomena occurred because 0.51 V/cm exceeded the field excitation threshold for the trabecular structure present in the reentrant path. Once this structure became excited, it was either depolarized or refractory when the reentrant wavefront approached the structure. Because this narrow path was necessary to maintain the reentry, the wavefront had no alternative route and terminated. An optical trace from the location indicated with a cyan box in FIG. 16a is shown in FIG. 16c and the corresponding surface ECG recording is shown in FIG. 16d.

Figure 17:
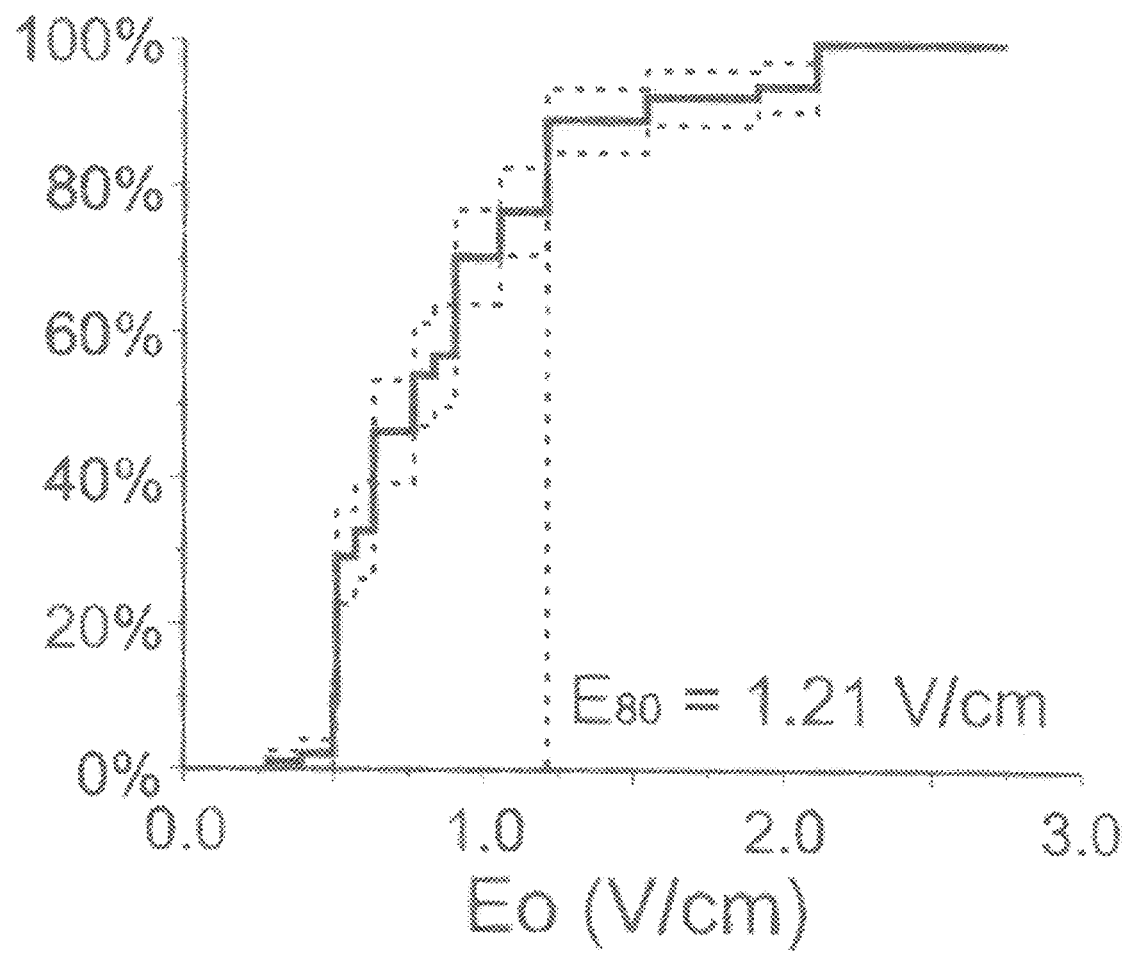
FIG. 17 is a graph of a survival analysis of terminated reentries versus shock strength.

In this study a total of 192 reentries were initiated and terminated or unpinned in 14 experimental animals. Across all animals, the average period of reentry was 155.78±38.58 ms. Survival analysis found that $E_{80}$ (shock strength at which 80% of reentries were terminated) was 1.21 V/cm which corresponds to 6.6 times the average field excitation threshold. A survival plot of the combined experiments is shown in FIG. 17, with the red dashed lines indicating the upper and lower 95% confidence intervals. All reentries in all experimental animals were terminated at shock strengths at or below 2.74 V/cm.

In the present study, a new method of low voltage destabilization and termination of ventricular reentrant tachyarrhythmias was investigated in an appropriate model of the infarction BZ. Two different mechanisms of unpinning and termination of reentrant arrhythmias were observed in this model; one of which was predicted by the theoretical investigations and one of which was not.

The infarction BZ model used in this study was critical for many reasons. First and foremost, immunohistochemistry results indicated survival of only 0.38±0.10 µm of the endocardial superfused surface. This thin layer of surviving tissue provided an essentially two-dimensional sheet of endocardium. This assured that the reentrant arrhythmia could be constantly visualized using optical imaging techniques as there was no transmural progression of the reentry into the mid-myocardial layers where optical imaging can no longer record changes in transmembrane potential. Also of great importance was the ability of this preparation to sustain stable reentrant arrhythmias. This was likely due to slight variations in the depth of the infarction BZ and levels of phosphorylated Cx43. Peters and colleagues observed that pathways of reentrant circuits and functional lines of block occurred in regions where the surviving layer of the infarction BZ was thinnest in a canine model of the epicardial BZ. (Peters N S, Coromilas J, Severs N J, Wit A L., "Disturbed connexin43 gap junction distribution correlates with the location of reentrant circuits in the epicardial border zone of healing canine infarcts that cause ventricular tachycardia," *Circulation*. 1997; 95:988-996)

In this study, two mechanisms of low-voltage destabilization of reentrant arrhythmias were observed in the superfused endocardial model of the infarction BZ. The first of these mechanisms was predicted with bidomain models of anatomically-defined reentry by the theoretical investigations where appropriately-timed VEP-induced excitation of the reentry core interacts with the reentry causing unpinning and possible subsequent termination. This mechanism was observed in all experimental preparations in the present study and is illustrated in FIGS. 14a-14e and FIGS. 15a-15f. After unpinning of the reentrant arrhythmia, the predominant result in this isolated ventricular free wall was termination of the reentry when it reached the edge of the preparation. However, this was not the only observed result and immediate termination would not necessarily be expected in a whole heart model. FIGS. 15a-15f illustrate an example where once unpinned, the reentry immediately repinned to another heterogeneity on the preparation. This behavior would be expected in a whole heart where much heterogeneity exists that could act to repin the reentry.

To avoid immediate repinning and facilitate complete termination of the unpinned reentry, one embodiment of the present invention uses anti-repinning (ARP) pulses applied after the low voltage unpinning shocks. Conventional ATP has difficulties terminating anatomical reentry when the pacing site is located at a distance from the reentry core. However, there are no such difficulties associated with ATP termination of a functional reentry. Therefore, once the reentry is unpinned from its anatomical core, ARP pulses can be effectively administered for terminating these now functional reentries and preventing their reattachment to a new core.

The second observed mechanism of low voltage termination occurred when the reentrant path included a small isthmus of tissue. These paths were present when the reentry was rotating near the edge of the isolated preparation, or when the reentrant path included a three-dimensional trabecular structure. In these instances, termination was always immediate; reentry was never effectively "unpinned," freely rotating about the tissue. The timing of shock application in these instances was not critical and exhibited a threshold-like behavior. Below a certain threshold, termination could not be achieved. However, above this threshold, termination could be achieved at all phases of the reentry period. An example of one such reentrant path along with successful and unsuccessful shock applications is illustrated in FIGS. 16a-16d. This mechanism of termination was observed for 4 different reentries in 2 different experimental animals. It is believed that both the threshold-like behavior and time-independence of this mechanism is due to the isthmus of tissue itself. The threshold of termination likely corresponds to the field excitation threshold of the isthmus. Shocks applied below this threshold will have little or no effect on the reentry. However, shocks applied above this threshold will excite the isthmus. Because the narrow isthmus is essential for maintenance of the reentry, when the reentrant wavefront reaches this now excited or refractory tissue, no other pathway exists for the reentry and it immediately terminates.

Regardless of the mechanism of unpinning and/or termination, the destabilization of a reentrant arrhythmia using this method can be achieved at significantly lower voltage gradients (VGs) than those required for conventional defibrillation. A recent study by Niemann and colleagues measured intracardiac VGs during transthoracic defibrillation, and found that for commercially available devices, intracardiac VGs can reach up to 33 V/cm for monophasic waveforms and up to 24 V/cm for biphasic waveforms. (Niemann J T, Walker R G, Rosborough J P, "Intracardiac Voltage Gradients during Transthoracic Defibrillation: Implications for Postshock Myocardial Injury," Acad Emerg Med. 2005; 12:99-105). Similar studies have yet to be performed for defibrillation shocks administered with ICDs, although it is generally well known that the goal for an ICD is to create VGs of at least 5-10V/cm and it is likely that the VGs would be of similar magnitude to transthorasic defibrillation and perhaps much larger near the shock electrodes where VGs are more than 20 times greater than the weakest VG more distant from the electrode. Although the concept of a "threshold level" for myocardial dysfunction is ambiguous, studies of the effects of strong shocks on papillary muscles and ventricular muscle fibers have found the thresholds for electroporation and subsequent arrhythmogenic responses in these tissues to be as low as 15 V/cm and 34 V/cm, respectively. (Kodama I, Shibata N, Sakuma I, Mitsui K, Iida M, Suzuki R, Fukui Y, Hosoda S, Toyama J. Aftereffects of high-intensity DC stimulation on the electromechanical performance of ventricular muscle. *Am J Physiol*. 1994; 267:H248-H258; and Li H G, Jones D L, Yee R, Klein G J. Defibrillation shocks produce different effects on Purkinje fibers and ventricular muscle: implications for successful defibrillation, refibrillation and postshock arrhythmia. *J Am Coll Cardiol*. 1993; 22:607-614).

The method of the present invention for low-voltage termination of reentrant arrhythmias may be free from these adverse side effects of high VG shocks. The accepted VG for conventional defibrillation shocks (to defibrillate 80% of the time) is 5.4±0.8 V/cm for a 10 ms monophasic waveform. (Zhou X, Daubert J P, Wolf P D, Smith W M, Ideker R E, "Epicardial mapping of ventricular defibrillation with monophasic and biphasic shocks in dogs," *Circ Res*. 1993; 72:145-160). If this is the minimum VG required everywhere in the myocardium, and if this shock is delivered from an electrode on the heart, one can again consider that VGs nearest the electrode will reach magnitudes of more than 20 times the weakest VG. This results in VGs of over 100 V/cm near the electrode, which greatly exceeds the threshold for electroporation and arrhythmogenesis in some cardiac tissue. In the present study, it was determined that 80% of initiated reentries could be terminated with a VG of 1.21 V/cm (10 ms monophasic waveform) when shocks were effectively applied at the correct phase within the period of reentry. This corresponds to a 20-fold reduction $(5.4/1.21)^2$ in defibrillation energy. This is likely to result in much less severe damage and resulting myocardial dysfunction.

The method of termination, low voltage unpinning shock in accordance with the present invention combined with ARP pulses may be a powerful new clinical tool for treating fast VT and fibrillation. The significant reduction of energy provided by this method may allow for painless defibrillation.

Recording of VEP induced by low voltage shocks is a challenge due to the relatively low signal-to-noise ratios of optical signals in this superfused preparation and to the low amplitude of the shock-induced VEP. Thus, the study was unable to directly measure VEP at tissue heterogeneities.

Unpinning shocks alone is not likely to effectively terminate VT or VF in the human heart due to the larger size of the heart. The preparations in the study were relatively small so that in 13 out of 14 preparations, unpinning resulted in quick drift of reentry toward the edge of the preparation and termination. This is an unlikely scenario in the large mammalian heart. The study did not address this limitation, which could be resolved by subsequent application of ATP as described elsewhere in this specification.

Figure 18A:
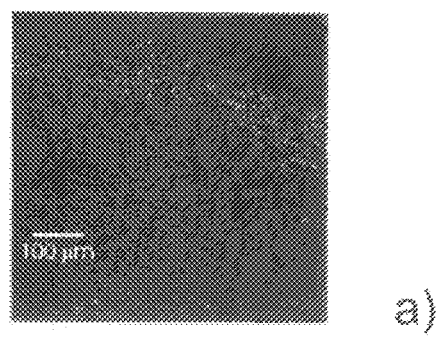
FIGS. 18a-18c are images of endocardial infarction border zone in acute and chronic models of infarction thin.
Figure 18B:
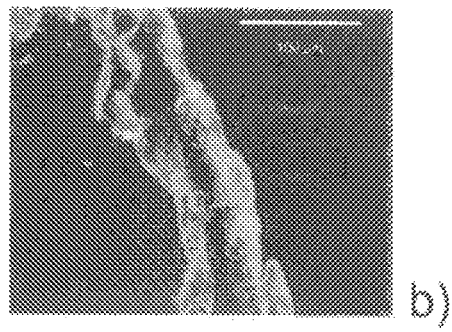
Figure 18C:

The experiments described above were conducted in superfused in vitro preparations in which only a thin endocardial layer survives after 30-40 minutes of ischemia of midmyocardial and epicardial layers as shown in FIGS. 18a-18c. This is a model of acute phase of infarction, in which arrhythmias are induced with significantly higher likelihood and reproducibility as compared to coronary perfused preparations or intact heart. Arrhythmia induction and termination is best in this preparation with some modifications because it offers the unique possibility to map electrical activity from entire available myocardium. However, it remains to be shown that arrhythmias could be reproducibly induced and mapped in hearts with chronic healed infarct. A preliminary study on a model of healed infarction, Li L, Nikolski V P, Wallick D W, Efimov I R, Cheng Y, Mechanisms of enhanced shock-induced arrhythmogenesis in the rabbit heart with healed myocardial infarction, Am. J. Physiol., 2005, revisions subm, the disclosure of which is hereby incorporated by reference herein, and which fully supported the hypothesis of the present invention.

Referring to FIGS. 18a-18c and FIGS. 19a-19d, in this model infarction was induced by ligature of left marginal artery during sterile surgery. Animals were allowed to recover for 1-8 weeks prior to in vitro study. As evident from FIGS. 18a-18c, direct perfusion from ventricular cavities allows survival of a thin layer of myocardium in the rabbit heart during acute phase and during healing of infarction. FIG. 18a shows anti-Cx43 staining reveals that only a thin 100-200 μm endocardial layer of cells, which remain coupled with gap junctional channel after 1 hour of ischemia. Deeper layers of cells uncouple due to dephosphorylation of Cx43. FIG. 18b shows triple immunostaining reveals that only a 2-cell thin layer of myocytes remains in this 4-week infarction border zone. As evident from Cx43 staining (red) these cells are coupled with gap junctional channels and are surrounded with large number of fibroblasts (blue). FIG. 18c shows histology Masson trichrome staining reveals that the entire endocardial layer of this massive infarct survives as a thin layer of endocardial border zone (EBZ). This section contains a free wall and a papillary muscle that were replaced with a scar during healing of infarction, except for 50-200 μm endocardial layers. No myocytes survived at the epicardium, which was entirely scarred.

Figure 19A:
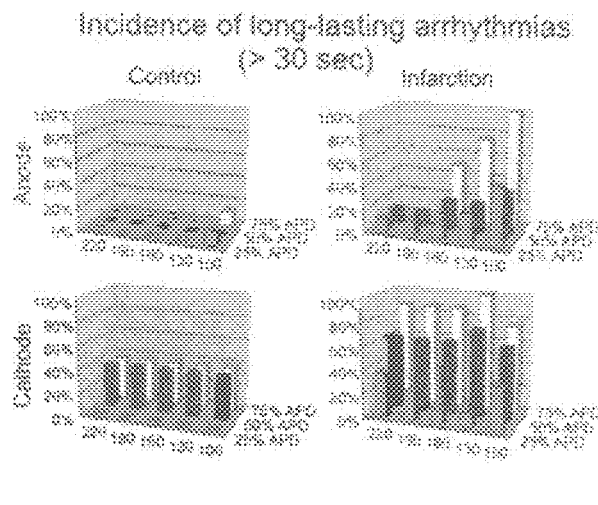
FIG. 19a is a series of graphs showing incidence and location of arrhythmias in a chronic infarction model.
Figure 19B:
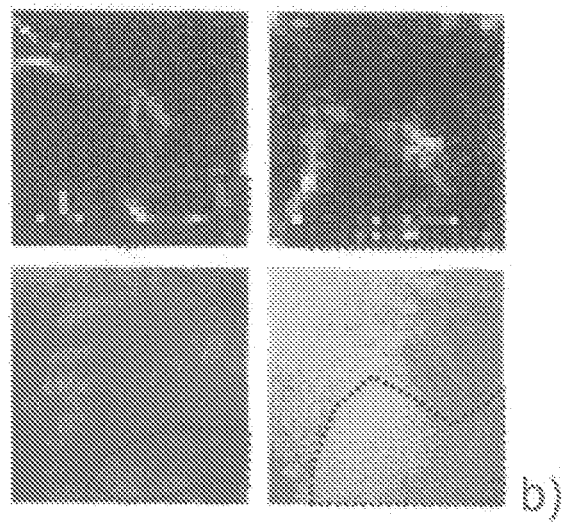

Preliminary data shows that this layer of tissue is responsible for a high propensity of arrhythmogenesis in agreement with studies by Peters et al in canine model of infarction. (Sambelashvili A., Nikolski V., Efimov I. R., Nonlinear effects in subthreshold virtual electrode polarization, Am. J. Physiol. Heart Circ. Physiol. 2003, 284(6):H2368-H2374). Data shows that expression of Cx43 is disrupted in this border zone (BZ) layer. Heterogeneities of Cx43 ion channel expression provide the ionic substrate for reentry. Another candidate is significant proliferation of fibroblasts, which could be coupled via gap junctions to the myocytes in the EBZ and thus alter source-sink relationship creating conditions for slow conduction and reentry. FIGS. 19a-19b illustrate significantly enhanced arrhythmogeneisis in this model (left panel) and the prominent role of the BZ layer in it. FIG. 19a shows vulnerability to arrhythmias was evaluated by monophasic shocks of either polarity applied at varying phase of action potential. Hearts with infarct were significantly more inducible. In FIG. 19b, the probability of reentrant wavefronts to occur at different anatomical locations is shown. Areas of infarction border zone were always involved in sustaining reentry.

Figure 20:
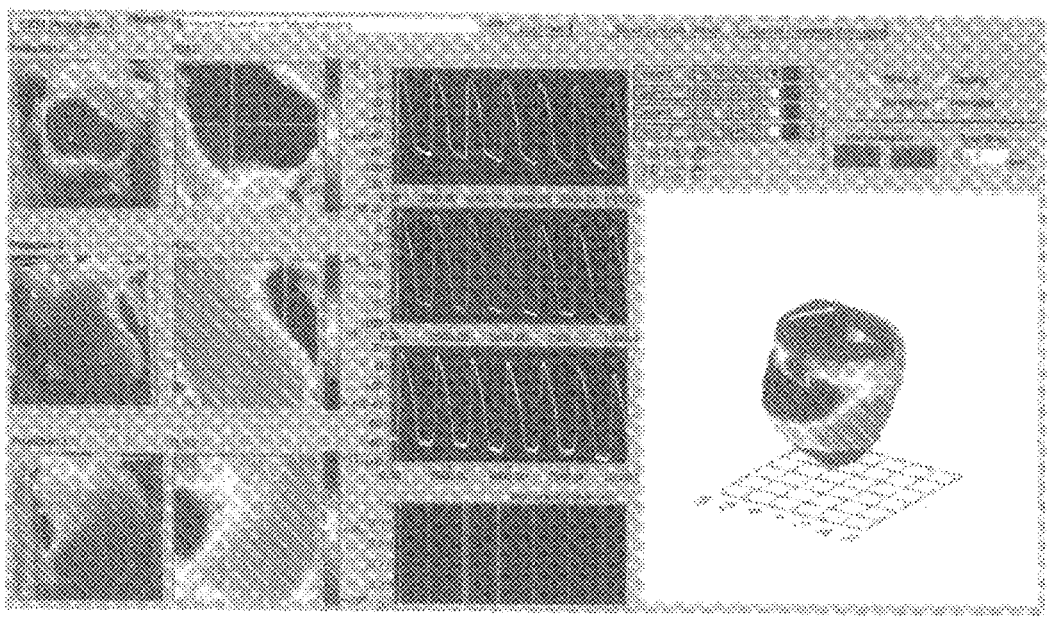
FIG. 20 illustrates preliminary results from a version of a model of the rabbit heart with acute and chronic states of infarction.

FIG. 20 illustrates preliminary results from a version of a model of the rabbit heart with acute and chronic states of infarction. 3D visualization of electrical activity in the Langendorff-perfused rabbit heart. Left three panels show three projections of the heart as they are seen by three photodiode arrays. Next three panels show maps of transmembrane potential recorded by corresponding PDAs. Next three panels show raw optical data $V_m$ recorded during sinus rhythm from recorded sites shown with circles in the left panels. Right lower panel shows 3D surface reconstruction of the heart and 3D distribution of transmembrane potential at a given time.

An elegant demonstration of the role of anatomical heterogeneities in the initiation and maintenance of reentry near the healed scar has been described in the literature. Sambelashvili A., Nikolski V., Efimov I. R., Nonlinear effects in subthreshold virtual electrode polarization, Am. J. Physiol. Heart Circ. Physiol. 2003, 284(6):H2368-H2374; and F. Aguel, J. Eason, N. Trayanova. Advances in modeling cardiac defibrillation, IJBC, 13:3791-3805, 2003 These and numerous preceding studies set the stage for understanding the role of structural and molecular remodeling at the infarction border zone (IBZ) in the stabilization of reentrant circuits at the IBZ. In one embodiment of the present invention, three models of different stages of infarction in the rabbit heart were developed, which allow accurate documentation of the reentrant circuit and its termination during defibrillation. These models include: superfused and coronary perfused isolated RV free wall preparation to model the acute phase of infarction, isolated preparation from hearts with healed myocardial infarction, and intact Langendorff-perfused rabbit heart with healed myocardial infarction. These three models allow the systematic study of the application of the method of the present invention with appropriate spatial-temporal resolution. In particular, it is believed that in the model of coronary disease utilized by the present invention, reentrant arrhythmias are stabilized and facilitated by scars and IBZ areas and that reentrant circuits can pin to the scar and form a leading center of VT or VF.

A significant body of literature has presented convincing evidence of virtual electrode polarization during high energy defibrillation shocks. See, M. Hillebrener, J. Eason, N. Trayanova. Postshock arrhythmogenesis in a slice of the canine heart, J. Cardiovasc. Electrophys., 14:S249-S256, 2003; N. Trayanova, R. Gray, D. Bourn, J. Eason. Virtual electrode induced positive and negative graded responses: New insights into fibrillation induction and defibrillation, JCE. 14:756-763, 2003; C. Larson, L. Dragnev, N. Trayanova. Analysis of electrically-induced reentrant circuits in a sheet of myocardium, Annals Biomed. Eng., 31:1-13, 2003; Efimov I. R., Fibrillation or Neurillation: Back to the future in our concepts of sudden cardiac death? Circ. Res. 2003, 92(10):1062-4. Editorial; Efimov I. R., Nikolski V. P., Diastolic shocking experience: do virtual anodes exist only during systole?, J. Cardiovasc. Electrophysiol., 2003, 14(11): 1223-4. Editorial; Efimov I. R., Biermann M., Zipes, D., Fast Fluorescent Mapping of Electrical Activity in the Heart: Practical Guide to Experimental Design and Applications. In "Cardiac Mapping", 2nd edition, eds. Shenasa M., Borggrefe M., Breithardt G., Futura Publishing Co., 2003, p. 131-156; and Cheng Y., Li L., Nikolski V. N., Tchou P. J., Efimov I. R., Shock-induced arrhythmogenesis is enhanced by 2,3-butanedione monoxime as compared with cytochalasin D, Am. J. Physiol., 2004, 286(1): H310-H318, all of which are incorporated herein by reference.

Imaging with voltage sensitive dyes has established that electric shocks produce simultaneously areas of positive and negative polarization. These areas of positive and negative polarization are commonly referred to as areas of virtual cathodes and virtual anodes, respectively. Polarity and strength of polarization is determined by the strength of the virtual electrode or "activating function", which depends on both the field strength and on the tissue resistive properties. Microscopic and macroscopic resistive heterogeneities are particularly important sources of virtual electrodes, because they strongly contribute to the generalized activating function via components of resistivity tensor, as described in Takagi S., Pumir A., Pazo D., Efimov I., Nikolski V., Krinsky V., Unpinning and removal of a rotating wave in cardiac muscle. Phys. Rev. Let., 2004, 93: 05810, the disclosure of which is hereby incorporated by reference herein.

The present invention further hypothesize that scars and other sources of resistive heterogeneity facilitate shock-induced polarization via the effect known as "virtual electrode" polarization or interchangeably "secondary source" formation. Thus, one embodiment of the present invention takes advantage of the fact that the same anatomical heterogeneities that facilitate sustained stable reentry also facilitate electric-field induced transmembrane polarization in adjacent areas of excitable myocardium. Based on this observation, it is believed that a low energy shock will selectively affect areas that provide the substrate for the leading center(s) of VT/VF. Therefore, we will be able to destabilize and terminate VT/VF with significantly lower energy as compared with conventional defibrillation, in which termination of activity in nearly all cardiac cells is required.

The present invention overcomes the reasons that previous attempts at ATP have not achieved effective unpinning of a reentry by recognizing that unpinning reentry does not necessarily mean its subsequent automatic termination. An unpinned anatomical reentry preferably must be terminated by another method. As previously described, in one embodiment of the present invention, anti-repinning (ARP) pulses generally analogous to anti-tachycardia pacing (ATP) pulses are employed immediately after the low energy pulse to terminate any unpinned reentry. Presently, low energy ATP is sometimes used as an alternative to high energy defibrillation shock. Current ATP therapy is applied prior to defibrillation shock at an empirically chosen frequency higher than that of VT/VF. A defibrillation shock is then used as a last resort when ATP fails, which occurs in 10-30% of cases. In this embodiment of the present invention, these two events are reversed: a low-energy unpinning shock is applied first and ARP termination of the unpinned reentry is applied second. Although ARP in accordance with the present invention is generally analogous to conventional ATP, the purpose and timing of ARP pulses is not to control heart rate as is the case for ATP pulses. It is believed that the combination of appropriately-timed low energy shock with ARP in accordance with this embodiment of the present invention will allow significantly reduce defibrillation energy requirements by increasing the efficacy of ARP pulses that are "preconditioned" with an unpinning shock. Preferably, the ARP pulses of the present invention will be delivered as near-field electrical stimulation pulses similar to pacing and ATP pulses. Alternatively, the ARP pulses of the present invention may be delivered as far-field electrical stimulation pulses.

Earlier studies of defibrillation have been impeded by the inability to observe electrical activity from the entire surface of the heart. Several research laboratories have attempted to develop panoramic imaging, which would allow dynamic detection of wavefronts of excitation from the entire epicardium of a Langendorff-perfused heart. Previous approaches employed CCD sensors, which typically produce lower signal quality as compared with photodiode array (PDA) sensors.

Figure 21:
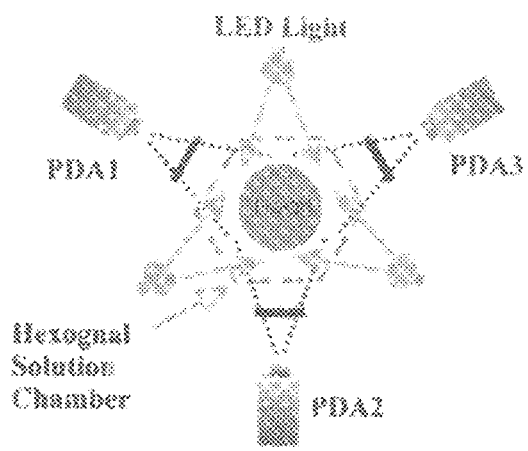
FIG. 21 shows a schematic diagram and photograph of a panoramic optical system.
Figure 21:
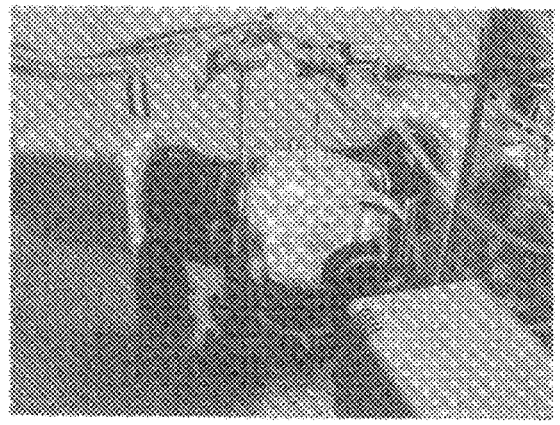

One embodiment of the present invention has utilized a PDA-based panoramic system with a high sampling rate (5000 frames/sec) and signal-to-noise ratio (78±21). This new imaging system has 768 individual optical channels (256×3) and 8 instrumental channels. We developed an integrated control software under LabVIEW (National Instruments) with an advanced custom-made toolbox for dynamic analysis and visualization of electrical activity on the entire epicardial surface. FIG. 21 shows a schematic diagram and photograph of the panoramic system. A 3D fast panoramic optical mapping system consists of 3 16×16 photodiode arrays (Hamamatsu) and 3 arrays of super luminescent light emitting diodes (LEDs). System allows continuous image acquisition of electrical activity at 5000 frames/second from the entire surface of the heart, stained with voltage-sensitive dye di-4ANEPPS.

The mechanisms of formation of the post-shock wavefronts, phase singularities, and scroll-wave filaments have been examined in Sambelashvili A., Efimov I. R., Dynamics of virtual electrode-induced scroll-wave reentry in a 3D bidomain model. Am. J. Physiol. 2004: 287(4): H1570-81, the disclosure of which is hereby incorporated by reference herein. It has been demonstrated for the first time how VEP induced phase singularity mechanism is responsible for I, U and O-shaped scroll wave formation in a simplified slab 3D active bidomain model. In several experimental publications we have examined factors responsible for survival of wavefronts of break excitation, which are formed by virtual electrode polarization. In particular, the role of sodium and calcium channels was examined as described in Li L., Nikolski V., Efimov I. R., The effect of lidocaine on shock-induced vulnerability. J. Cardiovasc. Electrophysiol, 2003, 14: S237-S248; and Mowrey K A, Efimov I R, Cheng Y, Kinetics of Shock Induced Transmembrane polarization: Effects of Nifedipine and lidocaine, 2005, Am. J. Physiol., subm, the disclosures of which are hereby incorporated by reference herein.

The role of shock waveform rate, and electrode configuration was also examined in Qu F., Zarubin F., Nikolski V. N., Efimov I. R., The Gurvich defibrillation waveform has lower defibrillation threshold than the Zoll waveform and the truncated exponential waveform in the rabbit heart, Can. J. Physiol. Phar. 2005, in press; Qu F., Li L., Nikolski V. P., Sharma V., Efimov I. R., Mechanisms of Superiority of Ascending Ramp Waveforms: New Insights into Mechanisms of Shock-induced Vulnerability and Defibrillation, AJP, 2005, revisions subm; and Li L, Nikolski V P, Wallick D W, Efimov I R, Cheng Y, Mechanisms of enhanced shock-induced arrhythmogenesis in the rabbit heart with healed myocardial infarction, Am. J. Physiol., 2005, revisions subm, the disclosures of which are hereby incorporated by reference herein.

In parallel, the mechanisms of scroll wave formation and termination in the 3D bidomain model of the intact rabbit heart were investigated to determine whether post-shock behavior is dependent on the number of pre-shock functional reentrant circuits, and if so, what mechanisms were responsible. Shocks were applied to a 3D bidomain slice to terminate either a single scroll wave (SSW) or multiple scroll waves (MSWs). The ED50 shock strength for SSW was found to be 13% less than that for MSWs indicating that a larger number of functional reentries resulted in an increased DFT. Understanding the complex spatiotemporal dynamics of post-shock activity in the heart is exceedingly difficult. In the next set of studies, non-linear dynamics tools were used to simplify this task. Specifically, post-shock activity was studied in terms of the post-shock phase singularities, which represent the organizing centers of reentrant activity. This provided a new opportunity to clarify the interaction of the shock with the pre-shock phase singularities, to evaluate how the shock itself induced phase singularities, and to examine the behavior of the post-shock singularities for failed and successful shocks. The goal of mechanistically examining the interaction of VEP with the phase singularity of a scroll wave (SW) rotating in a bidomain sheet of straight fibers was presented in T. Ashihara, T. Namba, M. Ito, T. Ikeda, K. Nakazawa, N. Trayanova. Spiral wave control by a localized stimulus: A bidomain model study, J. Cardiovasc. Electrophys., 15:226-233, 2004, the disclosure of which is hereby incorporated by reference herein. It was found that this interaction resulted in one of three possible outcomes: SW shift, SW breakup, and no effect.

In accordance with one embodiment of the present invention, it is recognized that conventionally used truncated exponential waveforms which are used in ICDs and some external defibrillators are not optimal. These waveform were developed based on hardware considerations dating 50 years back. Based on our studies we suggested in these publications that biphasic sinusoidal Gurvich waveform, as described in Qu F., Li L., Nikolski V. P., Sharma V., Efimov I. R., Mechanisms of Superiority of Ascending Ramp Waveforms: New Insights into Mechanisms of Shock-induced Vulnerability and Defibrillation, AJP, 2005, revisions subm, the disclosure of which is hereby incorporated by reference herein. Alternatively, an ascending biphasic waveform as described in Li L, Nikolski V P, Wallick D W, Efimov I R, Cheng Y, Mechanisms of enhanced shock-induced arrhythmogenesis in the rabbit heart with healed myocardial infarction, Am. J. Physiol., 2005, revisions subm, the disclosure of which is hereby incorporated by reference herein, may offer a 20-30% improvement in defibrillation energy requirements.

The central idea of this superiority is based on observation that the cellular membrane has a time constant in 1-7 ms range depending on the state of myocardium and pharmacological therapy. See, Mowrey K A, Efimov I R, Cheng Y, Kinetics of Shock Induced Transmembrane polarization: Effects of Nifedipine and lidocaine, 2005, Am. J. Physiol., subm. Thus, it cannot follow the rapid leading edge of the shock, which is usually in 1 microsecond range. As a result, application of a descending ramp or exponential waveform would result in incomplete utilization of delivered energy. Indeed, the membrane reaches its maximum polarization after a delay from the leading edge and then the charge dissipates by the end of first phase of the shock, because of decaying activating function of a descending waveform. In contrast, ascending waveform keeps increasing activating function through the duration of the waveform and membrane is polarized at its maximum at the end of the $1^{st}$ phase. Thus, maximum utilization of the delivered energy is achieved during first phase. The second phase will follow and terminate arrhythmogenic effects of the first phase.

The method described above is exemplary of the method of the present invention. The methods above may be accomplished by an external device or by an internal, implanted device. The methods above may be accomplished using any number and configuration of electrode arrangements, such as endocardial, epicardial, intravenous, implantable or external, or any combination thereof, to deliver electrical cardiac stimulation in accordance with the present invention. Multiple path electrode configurations as contemplated for use with some embodiments of the present as shown, for example, in U.S. Pat. Nos. 5,306,291 and 5,766,226, the disclosure of each of which are hereby incorporated by reference herein.

It is contemplated that the method of the present invention can be utilized together with, or separate from, other pacing and defibrillation therapies. For example, the present invention can be implemented as part of an ICD where a high voltage defibrillation shock can be delivered in the event that the method of the present invention is unable to successfully convert a cardiac arrhythmia. Alternatively, the present invention could be implemented as part of a conventional pacemaker to provide for an emergency response to a VT/VF condition in the patient that would increase the chances of patient survival. Still another embodiment of the present invention could be implemented as part of an automated external defibrillator (AED) as part of the application of external electrical therapy for emergency response to a cardiac arrhythmia.

The methods of the present invention also contemplate the use of any number of arrangements and configurations of waveforms and waveshapes for the electrical stimulation pulse(s). Known monophasic, biphasic, triphasic and cross-phase stimulation pulses may be utilized. In one embodiment, the use of an ascending ramp waveform as described in the article entitled "Mechanisms of Superiority of Ascending Ramp Waveforms: New Insights into Mechanisms of Shock-induced Vulnerability and Defibrillation," a copy of which is attached as Appendix A to U.S. Provisional Application No. 60/697,858, and the disclosure of which is hereby incorporated by reference herein.

The methods of the present invention also contemplate the use of any number of arrangement and configurations for the generation of the electrical stimulation pulse(s). While conventional high voltage capacitor discharge circuitry may be utilized to generate the lower energy stimulation pulse(s) in accordance with the present invention, it is also expected that alternative arrangements could be utilized involving lower voltage capacitor arrangements, such as stacked, switched or secondary capacitors, rechargeable batteries, charge pump and voltage booster circuits as described, for example, in U.S. Pat. Nos. 5,199,429, 5,334,219, 5,365,391, 5,372,605, 5,383,907, 5,391,186, 5,405,363, 5,407,444, 5,413,591, 5,620,464 and 5,674,248, the disclosures of each of which are incorporated by reference herein. Generation of the ARP pulses in accordance with the preferred embodiment can be accomplished by any number of methods, including known methods for generating pacing pulses. Similarly, any number of known techniques for cardiac arrhythmia detection may be used in accordance with the method of the present invention.

Various modifications to the method may be apparent to one of skill in the art upon reading this disclosure. The above is not contemplated to limit the scope of the present invention, which is limited only by the claims below.

The invention claimed is:

1. An implantable system for treating ventricular tachyarrhythmias, the implantable system comprising:
   a plurality of implantable electrodes; and
   an implantable therapy generator operably connected to the plurality of implantable electrodes, the implantable therapy generator programmed to:
      detect a ventricular tachyarrhythmia in a heart of a patient;
      establish a termination window associated with the ventricular tachyarrhythmia;
      deliver an unpinning shock via the plurality of electrodes to the patient within the termination window that generates a relatively low voltage field to create a depolarized region in the heart to extinguish the ventricular tachycardia by destructively interfering with a reentry wave associated with the ventricular tachyarrhythmia so as to effectively unpin the reentry wave,
      wherein the unpinning shock is delivered at an energy that is higher than conventional anti-tachycardia pacing pulses and lower than an expected lower limit of vulnerability of the patient for the ventricular tachyarrhythmia such that the relatively low voltage field created by the unpinning shock is sufficient to unpin the reentry wave from a location in the heart without increasing a risk of ventricular fibrillation.

2. The system of claim 1 wherein the implantable therapy generator is programmed to deliver multiple pulses for each unpinning shock, wherein at least two of the pulses are delivered through different electrode paths in order to present alternative wave fronts to the reentry wave so as to produce an equivalent of a vector rotating field to the reentry wave.

3. The system of claim 1 wherein the implantable therapy generator is programmed to deliver at least one anti-repinning pulse subsequent to delivering the at least one unpinning shock and within the termination window to extinguish the reentry wave that is unpinned from the location in the heart, the at least one anti-repinning pulse having an energy that is less than the at least one unpinning shock.

4. The system of claim 1 wherein the implantable therapy generator is programmed to define the termination window as a time period based on a frequency of the ventricular tachyarrhythmia.

5. A method for treating ventricular tachyarrhythmias in a patient, comprising:
   providing an implantable therapy generator including programmably-operably circuitry to be implanted in a patient and operably connected to a plurality of implantable electrodes; and
   configuring the programmably-operably circuitry of the implantable therapy generator to detect and terminate a ventricular tachyarrhythmia, including by:
      establishing a termination window associated with the ventricular tachyarrhythmia; and
      deliver an unpinning shock via the plurality of electrodes to the patient within the termination window that generates a relatively low voltage field to create a depolarized region in the heart to extinguish the ventricular tachyarrhythmia by destructively interfering with a reentry wave associated with the ventricular tachyarrhythmias so as to effectively unpin the reentry wave,
      wherein the unpinning shock is delivered at an energy that is higher than conventional anti-tachycardia pacing pulses and lower than an expected lower limit of vulnerability of the patient for the ventricular tachyarrhythmia such that the relatively low voltage field created by the unpinning shock is sufficient to unpin the reentry wave from a location in the heart without increasing a risk of ventricular fibrillation.

6. The method of claim 5 wherein configuring the programmably-operably circuitry of the implantable therapy generator to deliver the unpinning shock includes delivering multiple pulses for each unpinning shock, wherein at least two of the pulses are delivered through different electrode paths in order to present alternative wave fronts to the reentry wave so as to produce an equivalent of a vector rotating field to the reentry wave.

7. The method of claim 5 wherein configuring the programmably-operably circuitry of the implantable therapy generator causes deliver of at least one anti-repinning pulse subsequent to delivering the at least one unpinning shock and within the termination window to extinguish the reentry wave that is unpinned from the location, the at least one anti-repinning pulse having an energy that is less than the at least one unpinning shock.

8. The method of claim 5 wherein configuring the programmably-operably circuitry of the implantable therapy generator defines the termination window as a time period based on a frequency of the ventricular tachyarrhythmia.

9. A method for controlling an implantable therapy generator adapted to be implanted in a patient and operably connected to a plurality of implantable electrodes, the method comprising configuring the implantable therapy generator to:

detect a ventricular tachyarrhythmia in a heart of a patient;
establish a termination window associated with the ventricular tachyarrhythmia;
within the termination window, deliver an unpinning shock via the plurality of electrodes that generates a relatively low voltage field to depolarize a region in the heart for extinguishing the ventricular tachyarrhythmia by destructively interfering with a reentry wave associated with the ventricular tachyarrhythmia so as to effectively unpin the reentry wave,
wherein the unpinning shock is delivered at an energy that is higher than conventional anti-tachycardia pacing pulses and lower than an expected lower limit of vulnerability of the patient for the ventricular tachyarrhythmia such that the relatively low voltage field created by the unpinning shock is sufficient to unpin the reentry wave from a location in the heart without increasing a risk of ventricular fibrillation.

10. The method of claim 9 wherein configuring the implantable therapy generator to deliver the unpinning shock includes delivery of multiple pulses for each unpinning shock, wherein at least two of the pulses are delivered through different electrode paths in order to present alternative wave fronts to the reentry wave so as to produce an equivalent of a vector rotating field to the reentry wave.

11. The method of claim 9 wherein configuring the implantable therapy generator further includes delivery of at least one anti-repinning pulse subsequent to delivering the at least one unpinning shock and within the termination window to extinguish the reentry wave that is unpinned from the location, the at least one anti-repinning pulse having an energy that is less than the at least one unpinning shock.

12. The method of claim 9 wherein configuring the implantable therapy generator defines the termination window as a time period based on a frequency of the ventricular tachyarrhythmia.

* * * * *